US012093403B2

(12) United States Patent
Jarvis

(10) Patent No.: US 12,093,403 B2
(45) Date of Patent: Sep. 17, 2024

(54) SYSTEMS AND METHODS OF ACCESS VALIDATION USING DISTRIBUTED LEDGER IDENTITY MANAGEMENT

(71) Applicant: Tyco Fire & Security GmbH, Neuhausen am Rheinfall (CH)

(72) Inventor: Graeme Jarvis, Marblehead, MA (US)

(73) Assignee: TYCO FIRE & SECURITY GMBH, Neuhausen am Rheinfall (CH)

( * ) Notice: Subject to any disclaimer, the term of this patent is extended or adjusted under 35 U.S.C. 154(b) by 419 days.

(21) Appl. No.: 17/186,783

(22) Filed: Feb. 26, 2021

(65) Prior Publication Data
US 2021/0319116 A1    Oct. 14, 2021

Related U.S. Application Data

(60) Provisional application No. 63/009,238, filed on Apr. 13, 2020.

(51) Int. Cl.
| | |
|---|---|
| *G06F 21/60* | (2013.01) |
| *G06F 16/23* | (2019.01) |
| *G06F 21/62* | (2013.01) |
| *G07C 9/25* | (2020.01) |
| *G16H 10/60* | (2018.01) |
| *H04L 9/30* | (2006.01) |
| *H04L 9/32* | (2006.01) |

(52) U.S. Cl.
CPC ........ *G06F 21/602* (2013.01); *G06F 16/2379* (2019.01); *G06F 21/6245* (2013.01); *G07C 9/257* (2020.01); *G16H 10/60* (2018.01); *H04L 9/30* (2013.01); *H04L 9/3247* (2013.01)

(58) Field of Classification Search
CPC .............. G06F 21/602; G06F 16/2379; G06F 21/6245; G16H 10/60; G07C 9/257; H04L 9/30; H04L 9/3247
See application file for complete search history.

(56) References Cited

U.S. PATENT DOCUMENTS

| | | | |
|---|---|---|---|
| 10,475,272 B2 | 11/2019 | Campero et al. | |
| 10,606,224 B2 * | 3/2020 | Rumble | ................... G07C 9/28 |

(Continued)

FOREIGN PATENT DOCUMENTS

WO    WO-2021178112 A1 *    9/2021

OTHER PUBLICATIONS

F. Ghaffari, E. Bertin, J. Hatin and N. Crespi, "Authentication and Access Control based on Distributed Ledger Technology: A survey," 2020 2nd Conference on Blockchain Research & Applications for Innovative Networks and Services (BRAINS), Paris, France, 2020, pp. 79-86 (Year: 2020).*

(Continued)

*Primary Examiner* — Luu T Pham
*Assistant Examiner* — Paul J Skwierawski
(74) *Attorney, Agent, or Firm* — Foley & Lardner LLP

(57) ABSTRACT

An access validation device includes a user interface and one or more processors. The user interface includes at least one of a display and an audio output device. The one or more processors cause an identity wallet to generate a credential regarding a medical status of a user using credential data representative of the status received from a distributed ledger. The one or more processors cause the identity wallet to present an indication of the status using the user interface.

14 Claims, 22 Drawing Sheets

(56) References Cited

U.S. PATENT DOCUMENTS

| | | | |
|---|---|---|---|
| 10,923,216 | B1 | 2/2021 | White et al. |
| 11,432,149 | B1* | 8/2022 | Dhanoa .................... H04L 9/50 |
| 2009/0047923 | A1* | 2/2009 | Jain ........................ G16H 10/65 |
| | | | 455/466 |
| 2017/0195336 | A1* | 7/2017 | Ouellette ................ G06F 21/32 |
| 2018/0076962 | A1* | 3/2018 | Campero ........... G07C 9/00182 |
| 2018/0294052 | A1* | 10/2018 | Fishman ................ G16H 10/65 |
| 2019/0361917 | A1* | 11/2019 | Tran .................... H04W 12/108 |
| 2020/0279464 | A1 | 9/2020 | Llewelyn |
| 2021/0165811 | A1* | 6/2021 | Sizemore ........... G06F 16/3329 |
| 2021/0319864 | A1* | 10/2021 | Wisniewski ........... G16H 50/80 |
| 2021/0375408 | A1* | 12/2021 | Krueger ............... G06Q 20/401 |
| 2022/0237308 | A1* | 7/2022 | Caplovitz ................ H04L 9/50 |
| 2022/0345317 | A1* | 10/2022 | Ho ...................... G06F 21/6245 |
| 2023/0092685 | A1* | 3/2023 | Maher ................... G16H 10/60 |
| | | | 726/28 |
| 2023/0377700 | A1* | 11/2023 | Andreina ............... G06Q 10/00 |

OTHER PUBLICATIONS

U.S. Appl. No. 62/964,069 (Caplovitz '069) filed Jan. 21, 2020 (Year: 2020).*

Extended European Search Report on EP 21167839.6, dated Sep. 24, 2021, 9 pages.

Hernandez-Ramos, et al, "Sharing Pandemic Vaccination Certificates Through Blockchain: Case Study and Performance Evaluation," European Commission, Joint Research Center, Jan. 13, 2021, 10 pages.

\* cited by examiner

SYSTEMS AND METHODS OF ACCESS VALIDATION USING DISTRIBUTED LEDGER IDENTITY MANAGEMENT

CROSS-REFERENCE TO RELATED APPLICATION

The present application claims the benefit of priority under 35 U.S.C. § 119 to U.S. Provisional Patent Application No. 63/009,238, filed Apr. 13, 2020, which is hereby incorporated by reference in its entirety.

BACKGROUND

Access control can be performed to selectively permit users to access and move into spaces. For example, users can provide credential data that can be validated in order to be granted access

SUMMARY

At least one aspect relates to an access validation system. The access validation system includes one or more processors that cause a distributed ledger to generate a record data structure regarding a user, the record data structure comprising an attribute indicating a medical status of a user and output credential data representing the medical status.

At least one aspect relates to an access validation device. The access validation device includes a user interface and one or more processors. The user interface includes at least one of a display and an audio output device. The one or more processors cause an identity wallet to generate a credential regarding a medical status of a user using credential data representative of the status received from a distributed ledger. The one or more processors cause the identity wallet to present an indication of the status using the user interface.

At least one aspect relates to a method of validating access into a space. The method includes receiving, by an electronic device, a request to enter a space. The method includes identifying, by the electronic device, credential data indicating a medical status corresponding to a policy for entry into the space. The method includes outputting, by the electronic device, a credential representing the credential data.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

Figure 1:
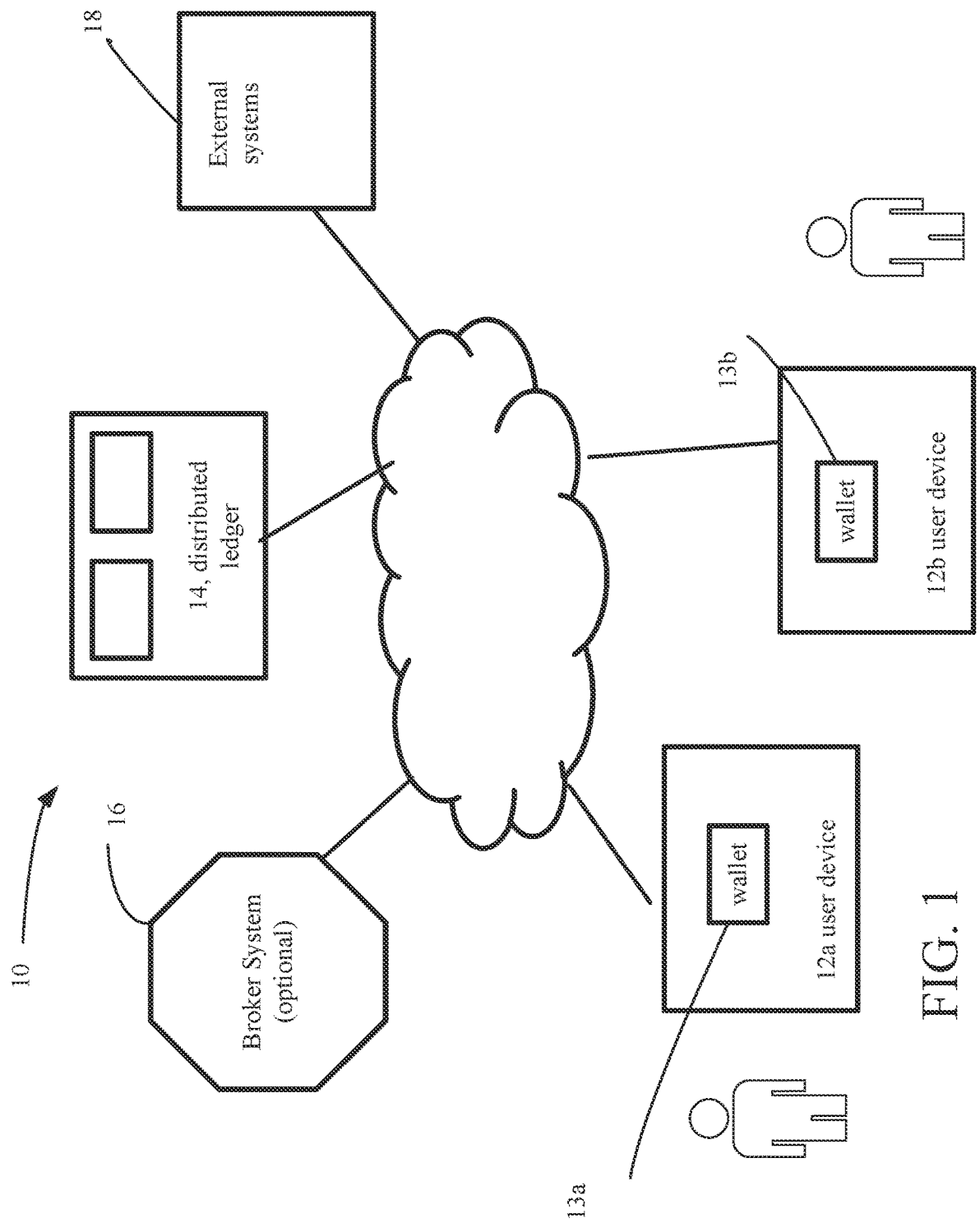
FIG. 1 is a schematic diagram of a system for securing PII information.

Access control systems can employ access cards or physical keys or physical fobs that include corresponding embedded electronic credentials that are read by a corresponding reader.

The access validation system can utilize a distributed ledger to generate a record data structure regarding a user and output credential data representing the medical status of the user. This is beneficial as by utilizing a distributed ledger, the access validation system can generate the record data structure more efficiently by reducing the number of intermediary information sources (e.g., human resources databases). The reduction of intermediaries reduces the amount of computational resources needed and reduces the complexity of data generation. This reduction in complexity can reduce the amount of power needed to complete the generation process as well as reduce the bandwidth necessary.

Computer systems can gather information, such as proprietary data on individuals. A type of information is proprietary data such as "personally identifiable information" commonly referred to as "PII." PII can include information of a sensitive, personal nature that is generally associated with individuals and is often protected by privacy laws in many jurisdictions. PII is information that can identify or contact or locate a single person or to identify an individual in context. Examples of PII include name, social security number, date and place of birth, mother's maiden name, biometric records and information that is linkable to an individual, such as medical, educational, financial, and employment information, as well as a user's device IP address used in a communication service broker.

Another type of information is proprietary data such as Machine Identifiable Information or "MII," such as in the context of the "Internet of Things." That is, other information that is collected includes operational information such as information used to control access control systems, intrusion detection systems and integrated security/alarm systems. For different reasons each of these types of information may have a sensitive nature that should limit the ubiquitous retention of such information in disparate systems.

Modern information technology and the Internet have made it easier to collect PII and MII through various mechanisms leading to various problems such as aiding of criminal acts, identity theft, etc.

Described herein is use of an IAM system (Identity and Access Management) that can be used for various forms of access validation. The IAM system can use a private service broker for dissemination of information such as PII (as well as other confidential information) between two or more electronic devices. The dissemination of information can occur in a controlled, secure and confidential manner. Also described is a mechanism that allows for the verification of information including PII (as well as other confidential information), and credentials, without the actual disclosure of the PII (as well as other confidential information).

User devices can be enabled to transmit PII (and other confidential information) without that information being hosted by third party (requesting systems) that would otherwise manage and store such PII (and other confidential information). Information can be hosted by third party systems or such information can be held by third party systems for attestation purposes, e.g., a registry that associates validation for access with particular users, such as a medical registry.

Systems and methods in accordance with the present disclosure can use application that in conjunction with the distributed ledgers can send to user devices containing a wallet a verified access or access error depending on the outcome of processing. All exchanges can be logged in the distributed ledger for audit tracking, etc. and verification of information can be used with information in the distributed ledger. Records can be added to the distributed ledger as transactions and include a hashed record of the transaction, what was exchanged, the signatures of the parties, and may include additional detailed information depending on the type of distributed ledger used.

FIG. 1 depicts a distributed network IAM system 10 (system 10) for access control and identity credential verification. The system 10 can use an Identity Wallet 13a, 13b with a distributed ledger 14 back-end (e.g., as compared to a centralized database (not shown)). The ID Wallet/distributed ledger approach provides enhanced user experience, security, compliance and so forth, as discussed below. The ID Wallet can replace and/or complement a physical access key or ignition key.

The system 10 includes user devices, here wireless enabled user mobile devices, such as smartphones 12a, 12b that operate respective identity wallets 13a, 13b. The smartphones 12a, 12b operate the identity wallets (also referred to herein simply as wallets) 13a, 13b, respectively and thus carry user credentials and by use of the wallet and a processor on the smartphone, interact with portions of the system 10.

A smartphone can be a mobile phone device that executes a mobile operating system. The smartphone can have hardware and a mobile operating system with features of personal computer hardware and operating systems along with features required for mobile or handheld operation, such as those functions needed for use of the smartphone as a cell phone and includes GPS (global position system) navigation. The smartphone executes applications (apps) such as a media player, as well as browsers, and other apps. Smartphones typically can access the Internet and have a touchscreen user interface. Other types of user devices could be used including personal computers, tablet computers, as well as, systems that are involved with exchange of sensitive data, such as access control systems and intrusion detection systems.

The identity wallet 13a can be implemented using a wearable device. Identity information can include biometric data. The identity wallet 13a can include an application that executes on an electronic device, such as the user devices 12a, 12b, and which allows a user of the device to store identity information, encrypt such identity information and communicate with external systems via communication functions/circuitry on the smartphone.

Identity Wallets 13a, 13b can authenticate credentials of the holder of the particular wallet, as well as other wallets and other systems/devices, as will be discussed below. A wallet can include or be associated with an arrangement of three systems: an electronic infrastructure, an application that operates with the system, and the device (e.g., smartphone) that operates the wallet. In the discussion below, the holder's proprietary data is associated with the wallet. For example, many pieces of identifying information can be stored in the wallet.

Such information can be diverse and wide-ranging, such as, bank account information, as well as the holder's information such as driver's license, health records, health care, loyalty card(s) and other ID documents stored on the phone, social security no., etc. All of this information can be stored in some manner and/or linked to the wallet. In particular stored in this wallet are pieces of information identifying the holders credentials, etc.

In the discussion below, in particular, the wallet 13a holds a user's credentials, such as for access to a vehicle or to a space or building in which entry is restricted based on medical statuses.

The system 10 can include a distributed ledger system 14. The distributed ledger system 14 can be a sequential, distributed transaction database. An example of a sequential, distributed transaction database is a "Blockchain" that operates with cryptocurrencies, such as "bitcoin"® (bitcoin project.org). The distributed ledger 14, rather than being dedicated to managing cryptocurrencies, can manage PII transactional records and other types of records, rather than cryptocurrencies, and can serve as the backend for a distributed access and verification system. The distributed ledger system 14 can interact with the user's wallet as well as third party systems to register users and allow user access to the vehicle or other restricted space.

The system 10 can include a service broker system 16 that is a third party service system that interfaces between the wallet 13a and the distributed ledger 14.

From the distributed ledger 14 encrypted PII data upon request can be transmitted to third party systems, as well as sending to third party systems listings of verifying systems, upon receiving access requests from the third party system. The service broker can include a hardware platform. For example, with a self-contained enterprise example, the service broker would include a hardware platform (e.g., a server computer system), a server operating system and a "calculator/attestor algorithm" (discussed below). The "calculator/attestor algorithm" would broker between the source and target peer-to-peer entities such that a minimal amount of information required to legitimize and execute an information exchange between the source and target is determined, exchanged, and validated so that a "transaction" can occur. The record of the transaction is written into the distributed ledger 14 with the minimum amount of PII or MII information, if any, including any metadata regarding the transaction or the information The system 10 can include external systems 18. In some examples these external systems 18 are third party systems 18a. The third party system 18a can be any electronic system (or device) and is the system/device that seeks some aspect of the PII or other confidential information of a user or held by the user device 12a, associated with the user. In the examples discussed below the external systems can be registration systems 18b, buildings or other spaces into which movement is restricted based on medical or medical conditions, or motor vehicles to permit physical access as well as control (starting) of the vehicle. Physical access can include access to a physical item, such as a motor vehicle, e.g., car, truck, etc. In the processes discussed below, some or all of the aforementioned user device 12a, wallet 13a, distributed ledger 14, optionally service broker 16 and third party access system 18 are used.

Driver Management

Various systems employed in vehicles contain dedicated microprocessors that run firmware to measure various parameters. For example, battery products are ever increasingly containing microprocessors that run firmware to measure battery load, voltage, temperature etc. and communicate directly with the main vehicle computer system.

Figure 1A:
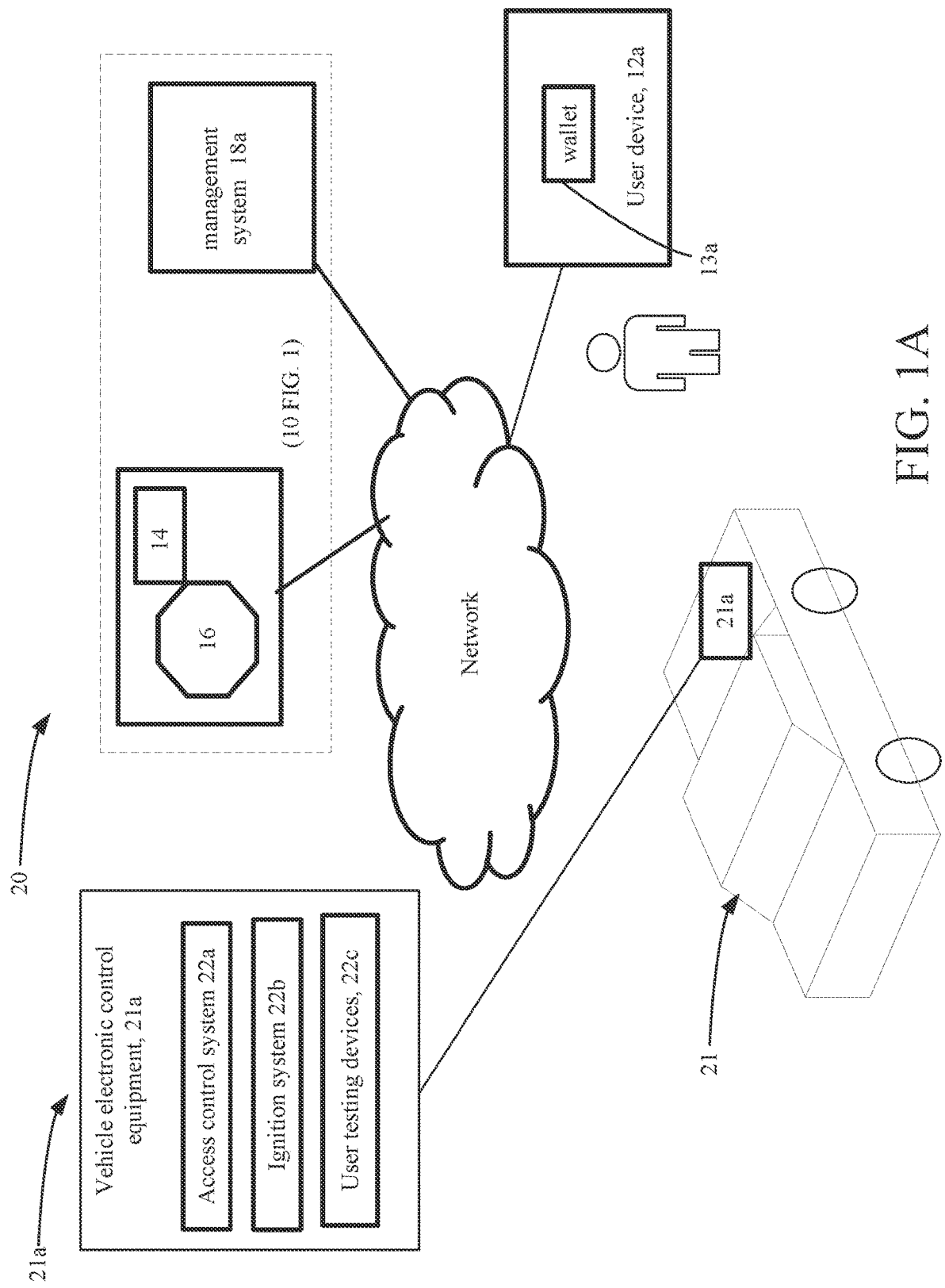
FIG. 1A is a schematic diagram of a system for access and operation management employing a PII system.

Referring now to FIG. 1A, a networked arrangement 20 for monitoring vehicle access and operation is shown. The arrangement 20 will be described in reference to accessing of a motor vehicle 21 such as a car. The arrangement involves vehicle electronic control equipment 21a that includes access control systems 22a, other vehicle systems such as those that monitor vehicle operation and environmental systems (not shown), ignition systems 22b to start the vehicle, and potential driver-testing devices 22c that test the status of the potential driver. Examples of potential driver-testing devices 22c include breathalyzer devices that analyze a potential driver's breathe to test the level of intoxication of the potential driver. Other potential driver testing devices 22c can be devices that measure an extent of other types of potential driver impairments to safe operation of the vehicle.

The arrangement 20 uses the distributed network IAM system 10 (FIG. 1) for access control to a vehicle. The arrangement 20 includes user devices 12 that are carried by the user that act as, e.g., a "virtual key" for entry into the vehicle. In the discussion below, an external system 18a is configured to determine whether a given user has privileges or authorization to enter and operate the vehicle. The arrangement also includes a specific one 12a of the user devices (generally 12) that houses the digital wallet (wallet) 13a, as discussed in FIG. 1.

Figure 1B:
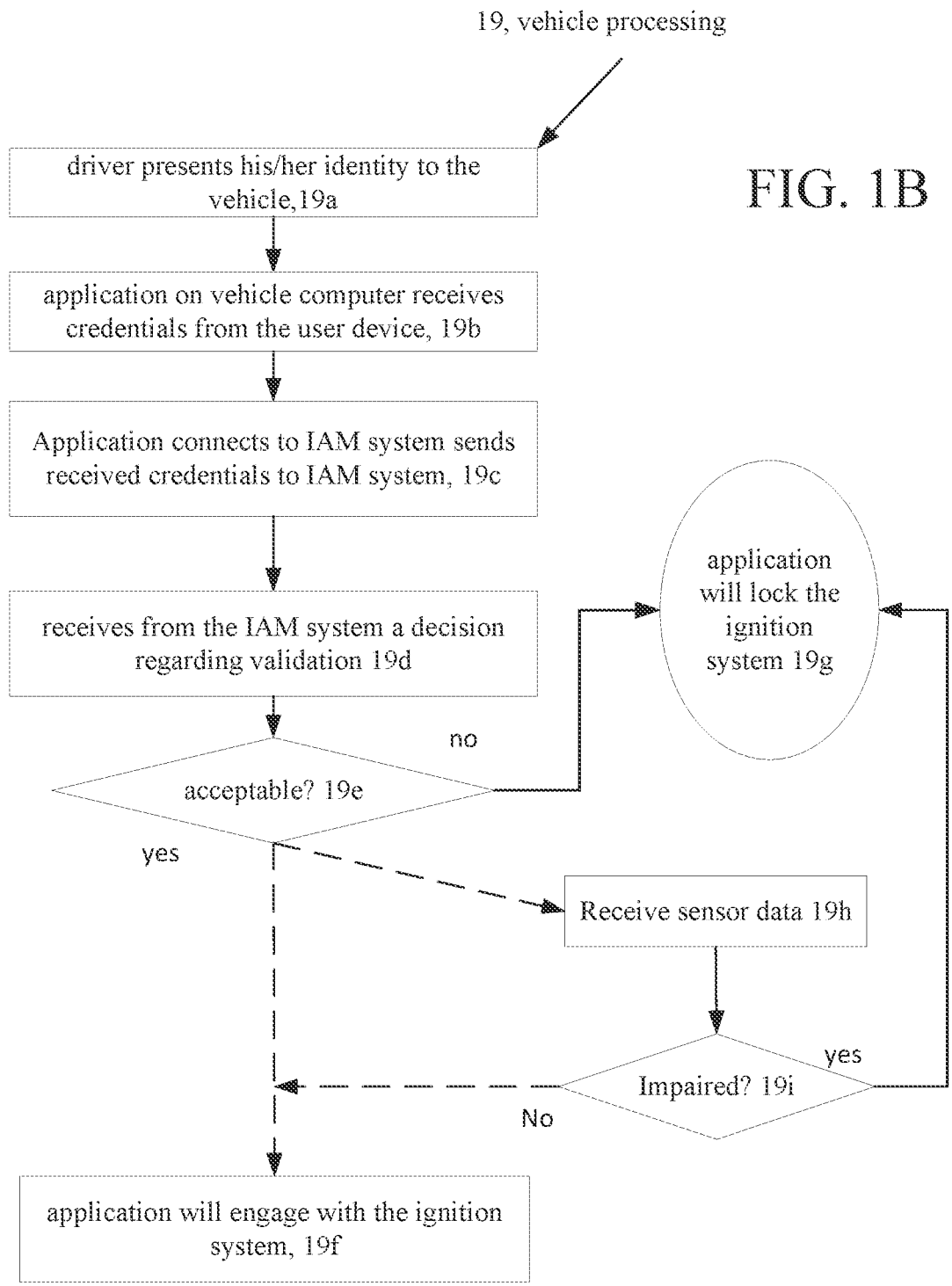
FIG. 1B is a flow diagram of PII-based access and operation management processing.

Referring now to FIG. 1B, an overall view of an embodiment 19 of the IAM system 10 used in conjunction with the vehicle 21, e.g., automobile is shown. When a potential driver enters the vehicle 21, the driver presents 19a his/her identity to the vehicle. The identity is presented through a wireless connection between an application on a user device such as the smartphone 12a to the IAM system 10. In one embodiment, the application is an identity wallet 13a on the smartphone 12a. A system executing an application on a vehicle computer (either the main computer system or another system such as a battery system), in the vehicle receives 19b credentials from the user device and connects 19c to the IAM system via an Internet connection. Examples of requested information include birth date, driver license number, home address etc. The IAM system is a specific implementation of a cloud based service that validates the driver's identity and whether the driver is authorized to drive the vehicle. This could be used, as one example, when employees of a company can only use the vehicle during specified hours on specified days and also determines the driver's identity, if the driver has the requisite training to operate the class of vehicle.

The application on the vehicle computer receives 19d from the IAM system a decision regarding validation of the received credentials of the driver. If acceptable 19e, the application in one embodiment will engage 19f with the ignition system of the vehicle to allow the driver to start the vehicle (shown as a dashed line). If not acceptable 19g the application will engage with the ignition system of the vehicle to block starting of the vehicle.

In some implementations, sensors can be deployed to sense presence of intoxicants 19h (alcohol or drugs, such as marijuana, etc.). That is, the system (either the main computer system or another system such as a battery system), in the vehicle can also be coupled to other sensors that gather data to be used to ascertain whether the potential driver is fit to drive the car. One example of such a sensor is a sobriety checking sensor. If impaired 19i application will lock the ignition system 19g. Otherwise, if not impaired, the application will engage 19f with the ignition system of the vehicle to allow the driver to start the vehicle (shown as dashed lines).

Thus, if the system determines that the driver is not authorized or is incapable of operating the car, the system will not start the car. In one particular example, the battery system determines fitness and will not provide power to start the engine should the potential driver be ascertained as unauthorized or unfit.

Figure 2:
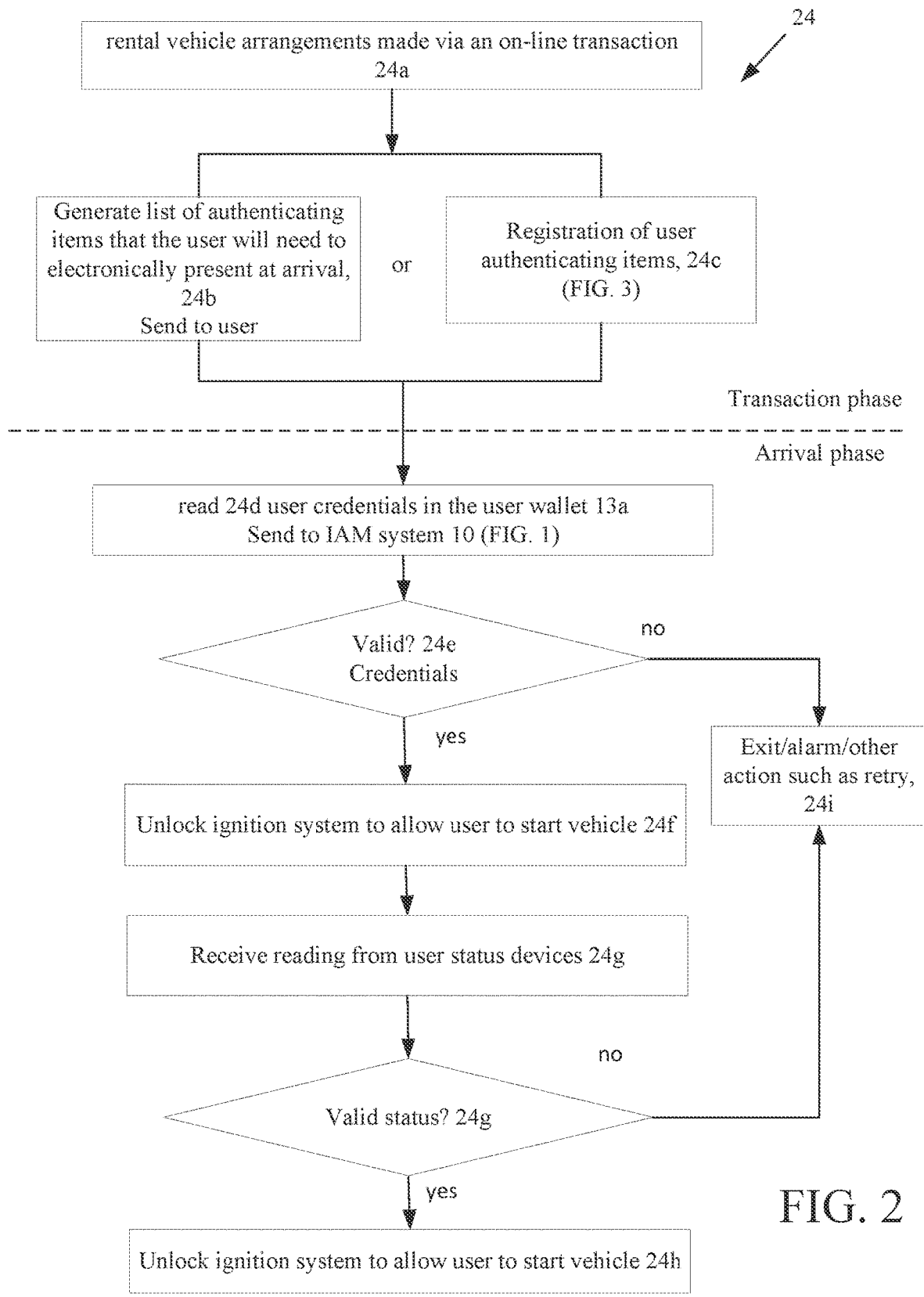
FIGS. 2-4 are flow diagrams of vehicle access and operation management processing.

Referring now to FIG. 2, a specific implementation 24 of the networked arrangement 20 for monitoring vehicle access is shown. In this arrangement, the vehicle is a rental vehicle and rental arrangements are made via an on-line transaction 24a. The details of the actual on-line transaction are not included in this discussion, as for the most part the details of the actual on-line transaction would be similar to those for conventional rental of a vehicle where a user presents a license, etc. at a rental agency counter. Suffice it here to say that the transaction includes a user making a reservation for a vehicle, paying for the vehicle via a credit card or other mode such as a virtual currency, e.g., Bitcoin, Ethereum, etc.

However, as part of the transaction upon completion of the reservation of the rental vehicle the arrangement either presents 24b a list of authenticating items that the potential driver will need to present electronically when the potential driver picks up the vehicle.

In an implementation that will be discussed in detail, below part of the transaction includes a registration process 24c to establish via the registration process 24c verified personal authenticating items in the potential driver's wallet. As part of the registration process 24c, (discussed in FIG. 3) the potential driver's device 12a, e.g., wallet 13a shares 24c with the IAM system 10 (FIG. 1), personal information that is validated 25b by the IAM system (i.e., with entities that are part of the distributed ledger 14 such as, for example, a governmental entity). Authenticating items will generally include a driver's license and/or one or more credit cards, including a credit card that the potential driver carries and which was used to pay for the rental, or in the case of use of a virtual currency a transaction record associated with the use of the virtual currency with payment of the rental and birth date, driver license number, home address etc. Other authenticating items could be used.

When a potential driver enters (or arrives at) the vehicle, the potential driver presents his/her identity to the vehicle through a wireless connection between an application on a potential driver device such as the smartphone 12a to the IAM system 10. The arrangement 24 uses the motor vehicle's 21 vehicle electronic control equipment 21a that includes the access control system 22a. The access control system includes in addition to conventional vehicle access systems, a credential reader (via wireless near field device technology) that reads 24d potential driver credentials in the user wallet 13a (in contrast to reading a manually entered code, or a code embedded in a physical key or a physical fob which are dedicated to such function, etc.). The identity wallet 13a on the smartphone 12a connects to a system in the vehicle, which executes an application. The system is in the vehicle. The system can be the main computer system or another system such as a battery system that includes a computing device. The system reads 24d the credentials from the potential driver device and connects to the IAM system 10 via an Internet connection and sends the read credentials for verification.

The system in the vehicle receives results 24f of the verification request from the IAM system 10. Upon verification 24f of credentials supplied by the potential driver's the arrangement 24 controls the ignition system 22b to allow the potential driver to enter and to start the vehicle. Upon entering the arrangement 24 can also use the motor vehicle's 21 vehicle electronic control equipment 21a to interface 24g with optional potential driver-testing devices 22c that test 24h the status of the potential driver. Either one or both can be used to controls the ignition systems 22b to allow the potential driver to start the vehicle. Also, verification can be used to allow the potential driver to merely start the vehicle or to enter and start the vehicle depending on implementation. Upon failure of verification 24i of credentials supplied by the potential driver's the arrangement 24 controls the ignition system 22b to allow the potential driver to enter and to start the vehicle.

Registration

Figure 3:
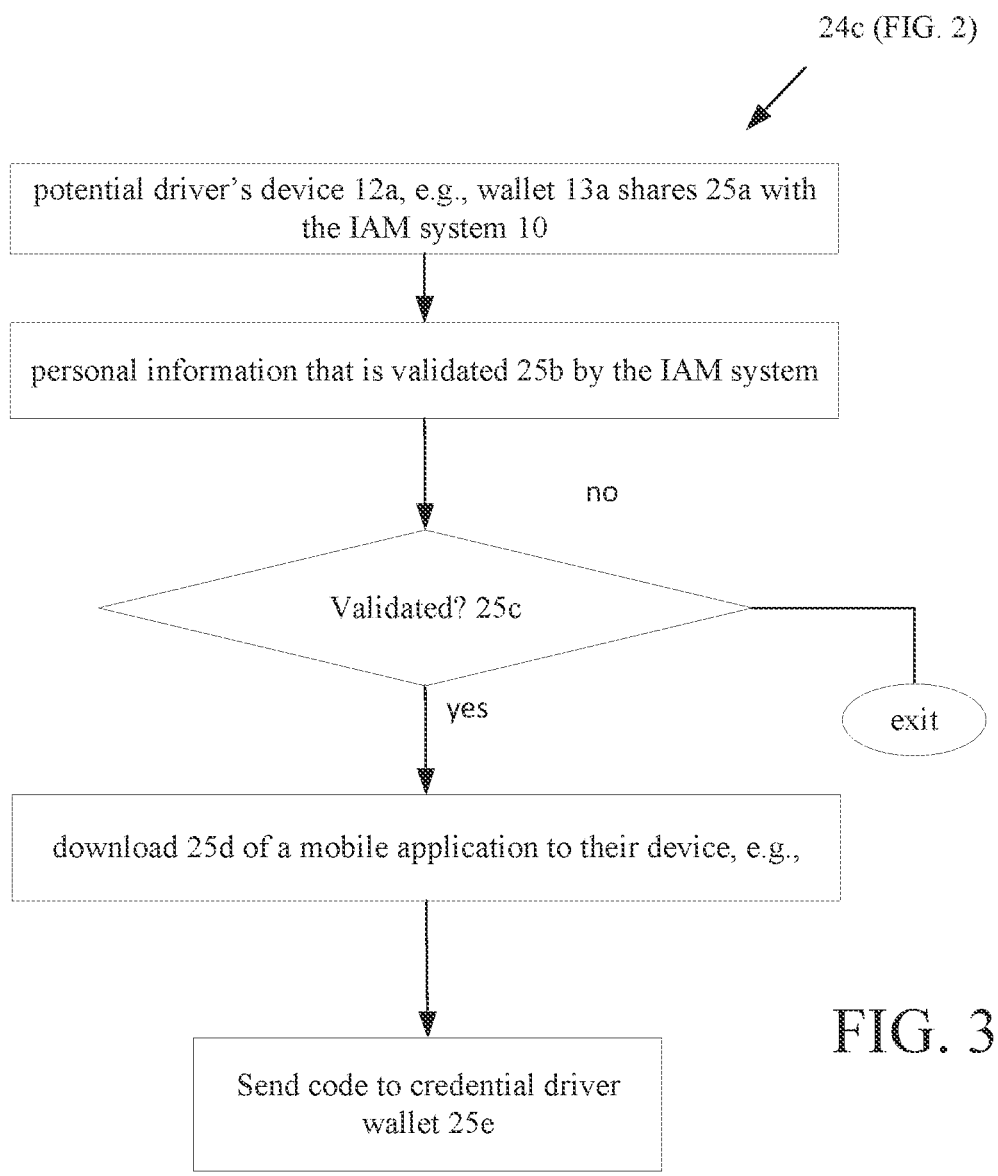

Referring now to FIG. 3, the registration process 24c (FIG. 2) uses the distributed network IAM system 10 (FIG. 1) to verify credentials in the user's wallet 13a, which effectively loads onto the user device 12 a key for entry into and starting of the vehicle. In the discussion below, an external system 18a is configured to determine whether a given potential driver has privileges or authorizations to enter and operate the vehicle. The arrangement also includes the user device 12a that houses the digital wallet (wallet) as discussed in FIG. 1. This registration process 26 could also be used at the time of potential driver arrival at the vehicle to satisfy the requirement of authenticating credentials that the potential driver will need to present electronically (see 24b, FIG. 2).

The potential driver can register, e.g., pre-register, with a system that performs rental and verification processing for a rental agency. Pre-registration can be before during or subsequent to completion of a rental transaction. As part of pre-registration, the potential driver's device 12a, e.g., wallet 13a shares 25a with the IAM system 10 (FIG. 1), personal information that is validated 25b by the IAM system (i.e., with entities that are part of the distributed ledger 14 such as, for example, a governmental entity). If validated 25d, the process 24c causes a download 25d of a mobile application to their device, e.g., smartphone 12a and the process tests 25d if a transaction was generated. If a transaction was not generated, the process 24c waits till the transaction is generated (or the process 24c can exit or take other action). When the transaction is generated, a QR code, or other electronic code is sent 25e to the potential driver's device 12a and/or wallet 13a. The QR code or other electronic code will include identifying code of the vehicle used for the rental transaction, as well as a location of the vehicle, description, etc.

Figure 4:
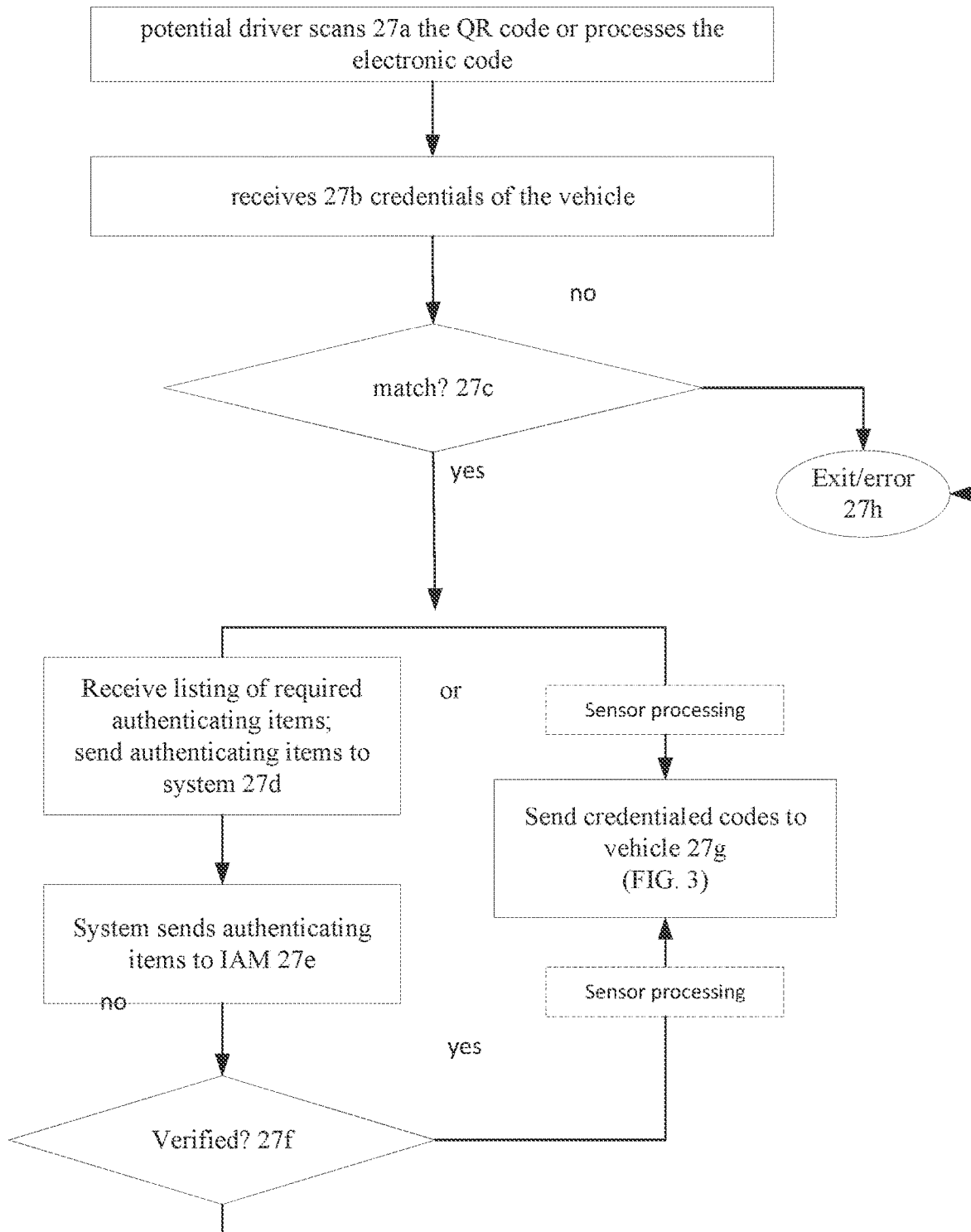

Referring now to FIG. 4, at check in the potential driver scans 27a the QR code or processes the electronic code. From the scan of the QR code (or processing of the electronic code) the device receives 27b credentials of the vehicle. The credentials of the vehicle are scanned and compared to credentials of the vehicle reserved for the user. If there is a match the user can share its credentials.

The device also receives 27c the listing of the personal information required. If the potential driver had not previously registered the wallet with its credentials with the system 27d, the listing will be displayed to the potential driver and will allow the user device upon verification of the credentials of the vehicle by the user device to release the personal information required from the user wallet. The system will send 27e the authenticating items to the IAM system 10. The process of FIG. 3 could be used/adapted for this verification.

If verified 27f, or if the potential driver had registered the wallet with its credentials with the system, e.g., during the transaction (FIG. 2, 24c), the wallet 13a (user device 12a) sends 27g the credentialed code to the vehicle. If the code is verified (FIG. 2, 24e), verification of the codes causes the vehicle to be unlocked and allows the potential driver to start the vehicle (e.g., pushbutton starting). If there is neither a match at 27c or verification at 27f, the process can exit, indicate an error or take other action 27h. In either case, release of personal information is according to the processes described below.

As mentioned, in some implementations sensors are deployed and sensor process (shown in phantom for both cases) is executed to sense presence of intoxicants (alcohol or drugs, such as marijuana, etc.) (see 19h, FIG. 2). That is, the system (either the main computer system or another system such as a battery system), in the vehicle ascertains whether the potential driver is fit to drive the car, as discussed above. Thus, if the system determines that the driver is not authorized or is incapable of operating the car, the system will not start and/or unlock the car, as appropriate.

Figure 5:
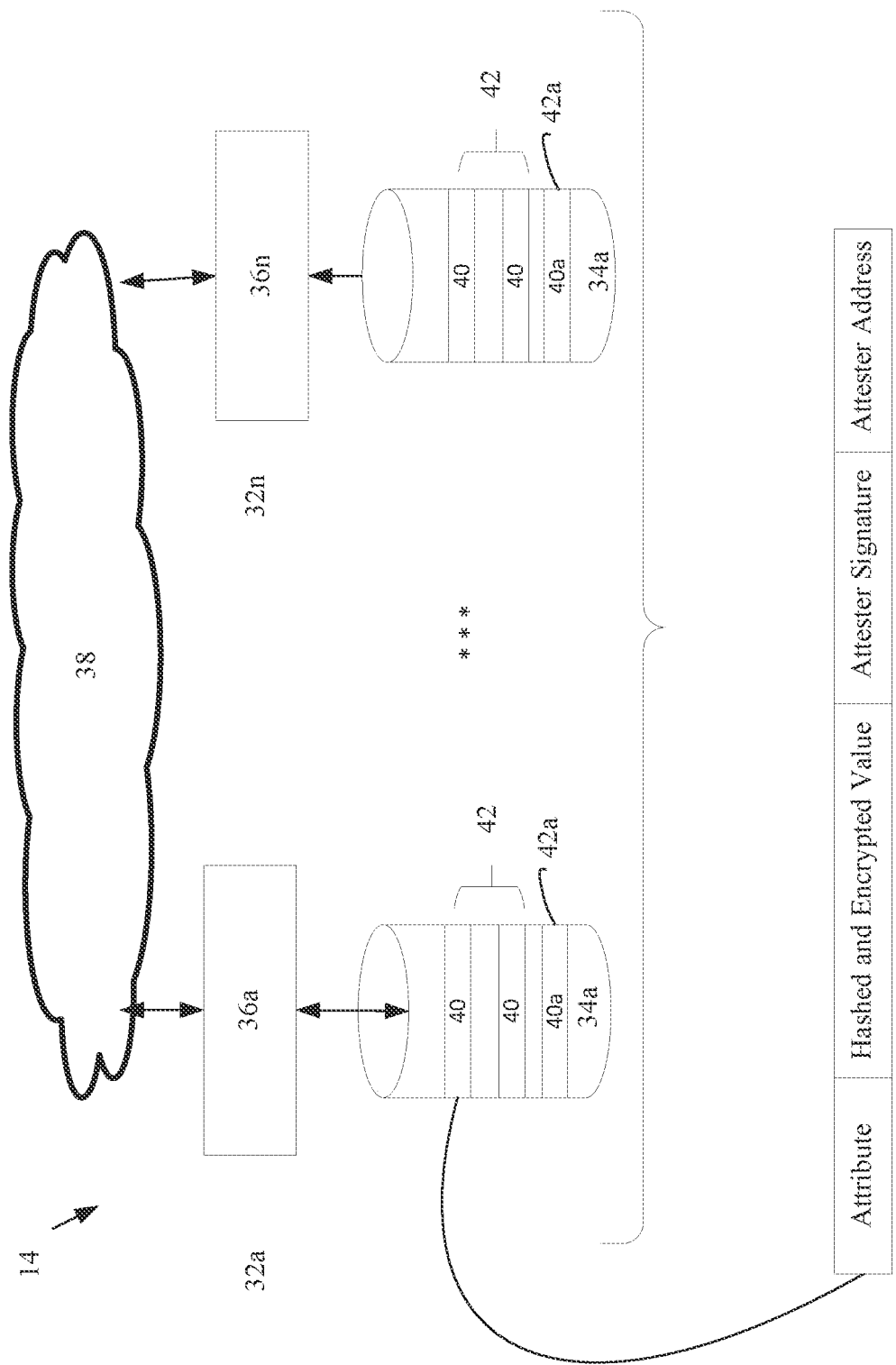
FIG. 5 is a block diagram of a distributed ledger.

Referring now to FIG. 5, the distributed ledger system 14 is shown. As mentioned, the distributed ledger system 14 is a sequential, distributed transaction database. The distributed ledger system 14 thus includes distributed databases 32a-32n that are typically existing in the "Cloud." The distributed database comprise storage devices 34a-34n that are attached to different interconnected computers 36a-36n. The distributed databases are controlled by a distributed database management system that controls storage of data over a network 38 of the interconnected computers and execute corresponding replication and duplication processes. Replication software (not shown) detects changes in the distributed database contents and once the changes have been detected, replicates the changes to have all the databases the same. Duplication software (not shown) identifies one database (not shown) as a master and then duplicates that database across other databases. Replication and duplication keep the data current in all distributed storage locations.

Each of the distributed databases 32a-32n that form the distributed ledger system 14 store encrypted information records. Typically the records will be a hash of an information record or a hashed pointer to an information record. In theory, assuming that the distributed databases 32a-32n could be hacked, a hacker will not access the actual data in information records, but only a hash of the actual data. An exemplary record 40 is shown below. The record 40 is stored in each of the distributed databases 32a-32n that form the distributed ledger system 14, which stores the record 40 in an encrypted form in the distributed ledger system 14. Record 40 has a structure that includes an attribute type, a hashed and encrypted value of the attribute, an attestor's digital signature of the hashed and encrypted value and the attestor's address. An exemplary record format is set out in table below.

| User Attribute | Hashed and Encrypted Value | Attestor Signature | Attestor Address |
|---|---|---|---|
| Attribute | encrypt(attribute) | Signature of encrypt(value) | Address |

An exemplary set of records is set out in table below. A set 42 of such records 40 can correspond to a user's profile. This set 42 (or profile) is added to with new records as new attributes of the user are added to the distributed ledger system 14.

| User Attribute | Hashed and Encrypted Value | Attestor Signature | Attestor Address |
|---|---|---|---|
| Citizenship | encrypt(USA) | Signature of encrypt(USA) | attst@cadmv.com |
| Current Age | encrypt(age) | Signature of encrypt(age) | attst@cadmv.com |
| Home Address | encrypt(address) | Signature of encrypt(address) | attst@cadmv.com |
| Height | encrypt(height) | Signature of encrypt(height) | attst@cadmv.com |
| Access credentials | encrypt(credentials) | Signature of encrypt(credentials) | secure@serv.com |
| * | * | * | * |
| * | * | * | * |
| * | * | * | * |

One can readily observe that what is stored in the distributed ledger system 14 is information about a user's attribute, a hash of that attribute, information about an attestor to the attribute, which information is attestor signature system, and attestor address. The attestor when contacted can attest to the requested information being valid. For example, given a user's birth certificate that is issued by a state governmental agency that state governmental agency converts the birth certificate to a digital file of the document, and that digitized file of the document is hashed to provide a hash of the digitized birth certificate document. Rather than the document itself being stored (or the digitized document being stored), what is stored is the hash of the digitized birth certificate document, that is stored in a user's profile in the distributed ledger 14.

Within a domain, distributed ledgers exchange information to maintain identical ledgers, with any suitable so called sequential transaction database technology of which "Blockchain" technology is but one example. However, unlike some electronic currency based technologies, e.g., bitcoin, where the Blockchain is designed so that no entity controls the Blockchain in some examples disclosed herein using the techniques disclosed herein the transaction database technology actually exchanges information within a domain and because such domains could be private transaction databases, each entity or industry could structure the transaction database as different private transaction databases.

Figure 6:
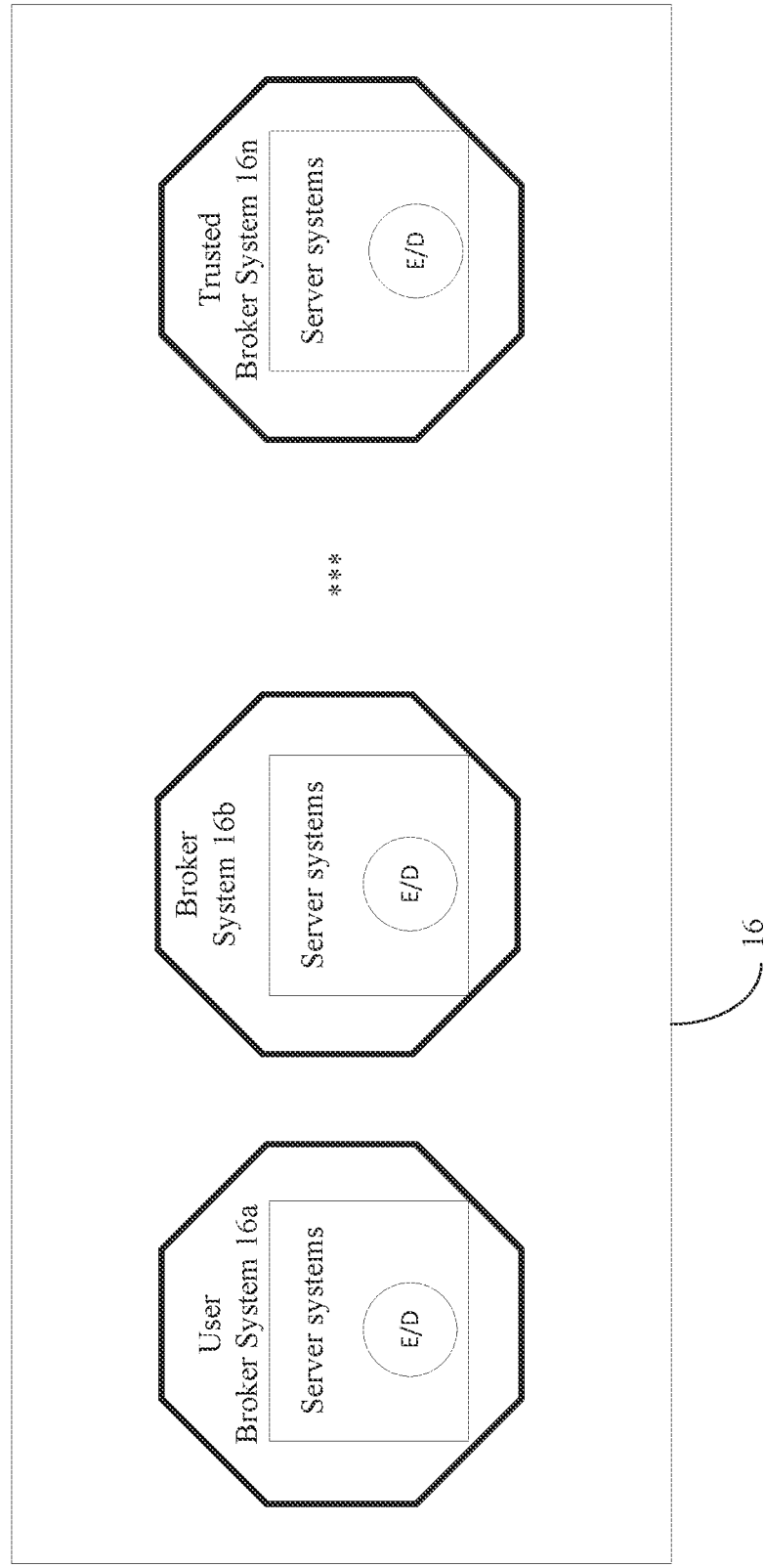
FIG. 6 is a block diagram of a broker system.

Referring now to FIG. 6, the broker system 16 is shown. The broker system 16 includes a computer system and executes software that handshakes between the user device 12 and the vetting agent or attestor. Rather than the user device 12a accessing the distributed ledger 14, all requests for transactions between the user device and the requesting device can occur through the broker system 16. For some transactions, the broker system 16 accesses the distributed ledger system 14, whereas in other transactions the requesting system 18 accesses the distributed ledger system 14.

As shown in FIG. 6, the broker system 16 can be a compilation of many such broker systems 16a-16n. Each of the broker systems 16a-16n can comprise computer systems and associated distributed databases. The broker systems 16a-16n are distributed over a network of servers that act together to manage the distributed ledger 14. All attribute hashed values, attestor information, etc. are stored in the distributed ledger 14 and as the flow diagram below will show the broker systems 16a-n are configured to access the distributed ledger 14 to obtain and validate such information. Also shown in FIG. 6, are the encryption and decryption (E/D) of data flows that take place between the broker systems 16a-n and wallets 13a.

Note that in the context of a private distributed ledger environment, for an enterprise, it may be desirable to not have a query sent to the attestor database for each transaction. Rather, a business rule could be established that once a validation event has occurred, then it is good for a period of time, until the attestor database is updated etc., so as to reduce latency.

Figure 7:
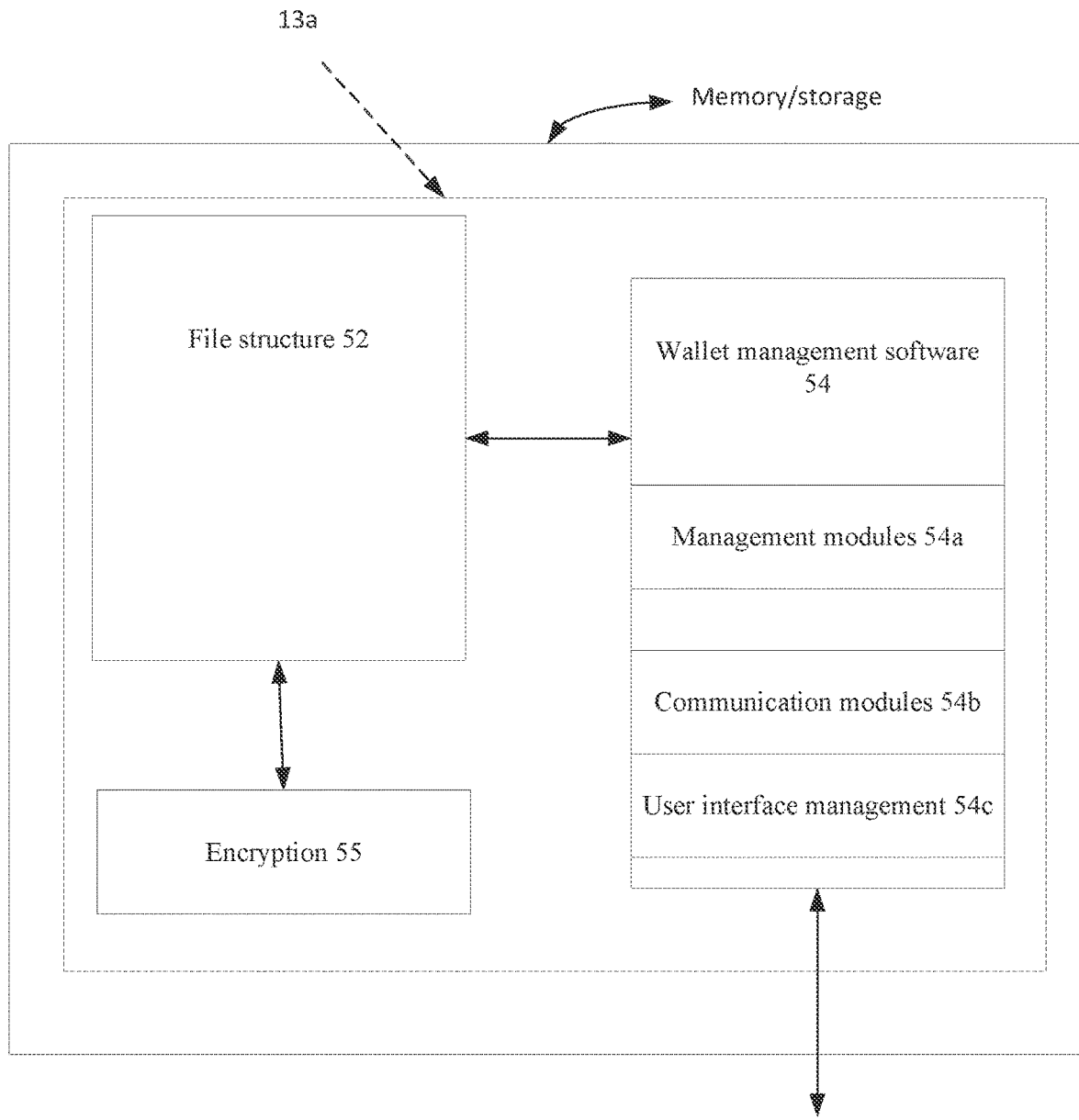
FIG. 7 is a block diagram of an identity wallet.

Referring now to FIG. 7, the wallet 13a is shown. The wallet 13a includes a file 52 structure and wallet management software 54 that are stored on a user device 12a (FIG. 1). In addition to the software comprising management modules 54a that handle request and access to the file structure, as well as receiving user authorizations, etc., the software also includes communication modules 54b that exchange information between the wallet and requestor systems, and between the wallet and the broker system 16 (when used) and that receives requests for information that result in messages being displayed on the user device 12a.

The wallet 13a stores information for handling a third party request for data directly from a user that transmits that information directly from the wallet 13a to the third party system 18 in a secure manner. The wallet 13a may take several form factors—a physical ID Wallet such as a credit card, smart wearable etc. or it may only need to be the software payload that a system pushes out to a commercially acceptable mobile device such as a smartphone. In some implementations, the wallet needs to be in communication with a device that can perform calculations/determinations, as will be discussed below.

The wallet 13a has the management module 54a that handles third party requests for information and/or attributes and the communication module 54b that interfaces with the broker system 16. The wallet 13a includes a module 54c that allows a user to view the request and either approve, all or part of none of the request. Upon approval (partial or all) of the request, the wallet 13a encrypts via encryption module 55 the requested information using a public key infrastructure (PKI) where a public key of the third party is used along with one the private keys associated with the wallet 13a to encrypt the data. The encrypted data can either be sent to the user's broker system 16 or the wallet 13a can look up the direct address of the third party system 18 and send the encrypted data directly to the third party system 18, depending on the implementation of the system 10.

A public key infrastructure (PKI) is a set of hardware, software, people, policies, and procedures needed to create, manage, distribute, use, store, and revoke digital certificates and manage public-key encryption. The purpose of a PKI is to facilitate the secure electronic transfer of information for a range of network activities such as e-commerce, internet banking and confidential email. PKI is required for activities where simple passwords are an inadequate authentication method. In cryptography, PKI binds public keys with respective user identities by means of a certificate authority (CA) within a CA domain. The user identity is unique within each CA domain.

Figure 8:
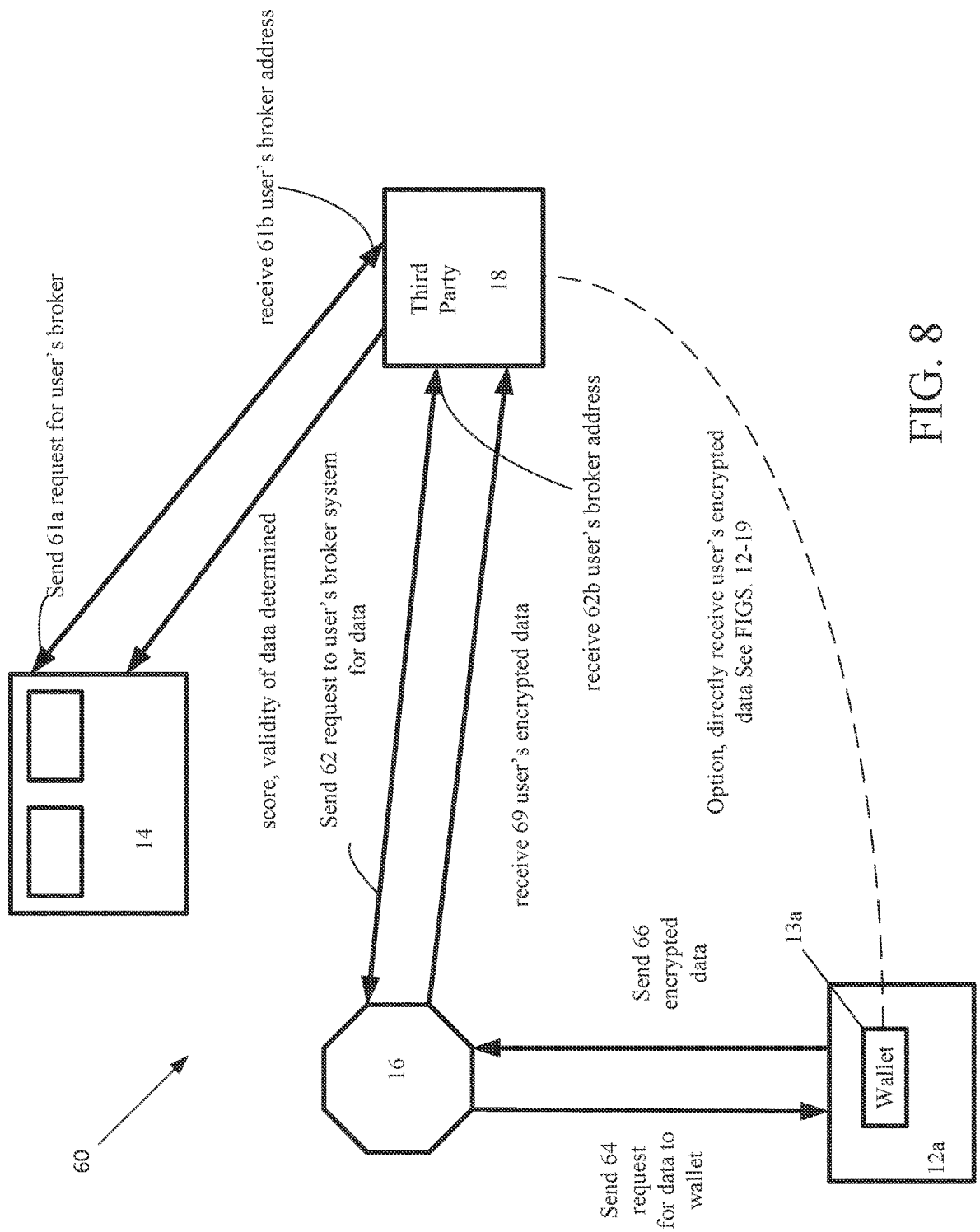
FIGS. 8-10 are block diagrams for message exchange processes.

Referring now to FIG. 8, a diagram of a process 60 and flow for the process 60 where the system 18*a* requests information from the user device 12*a*. In this case, the broker system 16 provides an asynchronous transfer between the user device 12*a* and the third party system 18. The third party system 18 sends a message request 61*a* to the distributed ledger 14 for the user's broker system. In general, there can be many such broker systems associated with many users. The third party system 18 receives 61*b* a message that includes an address of the user's determined broker, as received from the distributed ledger. (In the following figures, as needed, double arrowed lines and reference characters on tips of such arrows are used to denote paired messages, such as sending and receiving messages.) In other implementations, the address lookup can also go through the exchange network.

In an implementation that uses a broker, the third party system 18 (system discussed below) sends 62 a message to the user's determined broker 16, which message includes a request to access data on the user's wallet 13*a*. The request for data is sent 64 from the broker system 16. A "score" is calculated for determining the validity of the data (rather than being a measure of the secure transmission of the data). A scoring algorithm can be based on the number and types of attestors, etc., to the user's wallet 13*a* on device 12*a*. Various algorithms can be used such as one that weights types of attestors and number of attestors and normalized these to a standard. Thus, a score generated with a large number of highly trusted attestors would be higher than a score generated with a large number of attestors having a low level of trust. An alternative to this type of score is an attestor score based on the type of attestor and how trustworthy the attestor is and has been. For example, see the following table.

| Score | Number of attestors of high trust | Number of attestors of moderate trust | Number of attestors of low trust |
|---|---|---|---|
| 0-10 | 0 | 0 | No more than X |
| 11-20 | 0 | 0 | Greater than X less than Y |
| 21-40 | 0 | At least M | * |
| * | * | * | * |
| * | * | * | * |
| * | * | * | * |
| 91-100 | At least Z | | |

One algorithm, as in the table above, is a mapping scheme that maps a score range (or values) to various slots based on empirically determined number of attestors (M, X, Y, Z) and empirically determined trust levels (high, moderate, low). This could be an example of a score for an item. Thus, with an item could be stored the number of and types of attestors of various categories (three of which, low, moderate and high trust levels being shown) or the score range or value.

Other scoring algorithms such as weighted algorithms could be used, such as one of the form:

$$\text{Score}=((H*W_h+M*W_m+L*W_h)/\text{total})/\text{Normalized}$$

Where H is the total of high trusted attestors
M is the total of moderately trusted attestors
L is the total of low trusted attestors
$W_h$; $W_m$; $W_h$ are empirically determined weights, and Normalized is an optional normalization function or value.

The user's wallet 13*a* (or other application or user via a physical action using a user input device) either answers (yes or no) or simply ignores the message. When the answer is yes, the user's wallet 13*a* (or other application) encrypts the data using an asymmetric encryption algorithm that uses the requestor's public key. The encrypted data is sent 66 from the user's wallet 13*a* to the broker system 16 so that only the two endpoints (user's wallet 13*a* and the third party system 18) can read the actual data. At the broker 16 system, upon reception of the encrypted data from the user's wallet 18*a*, the broker system 16 sends the data to the third party system 18.

In another implementation, the data would be sent directly to the requestor's wallet without the broker system 16. This implementation can be especially used with the processes discussed below. In the processes below, this direct approach is used in the explanations of those processes.

Figure 9:
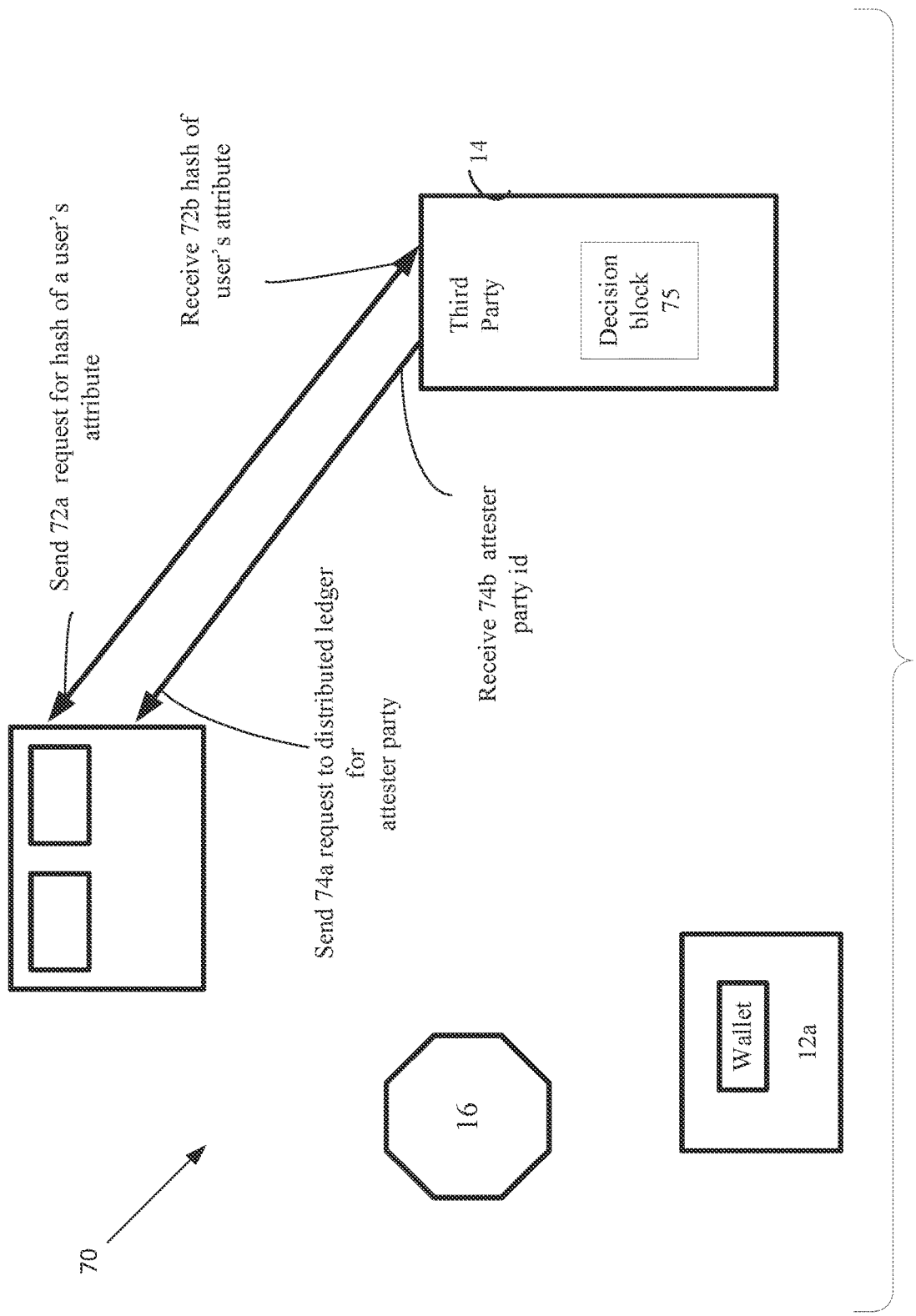

Referring now to FIG. 9, another process 70 is shown in which there is a required validation of PII data through a distributed public ledger 14*a*. The distributed ledgers can be public, meaning that anyone can place and/or access data in the ledger or private, meaning that only authorized individuals and entities can place and/or access the private type of ledger. Thus, generically, such distributed ledgers 14 can be public or private depending on various considerations. In either instance, the ledger 14 contains the information needed to validate the brokered information. The third party system 18 sends 72 a lookup request to the distributed ledger 14*a* for a particular user's attribute.

In FIG. 9, the broker 16 and wallet 13*a* and user device 12*a* are not directly involved, but are shown. The lookup request is actually for a hash of the desired user's attribute. The distributed public ledger 14*a* receives the request and accesses the hash of the particular user's attribute and returns 72*b* that hash to the third party system 18. The third party system 18 sends 74*a* a look up message request for the system that has attested to the hash of the particular user's attribute stored in the distributed public ledger 14*a*. The third party system 18 receives 74*b* the identity of the system that performed the attestation to the hash of the particular user's attribute, and makes an independent decision 75 on the validity of the hash of the particular user's attribute. For cases where privacy of the data is a concern this case assumes that the third party system has the user's public key, as the attribute data is encrypted. For other types of data where privacy of the data is not a concern, the attribute need not be encrypted.

Note, in addition to returning the attestor information, the system could return the attestor score of that attestor having the highest score. The score could be calculated by the distributed ledger 14, but may be more appropriately calculated by the broker system.

Figure 10:
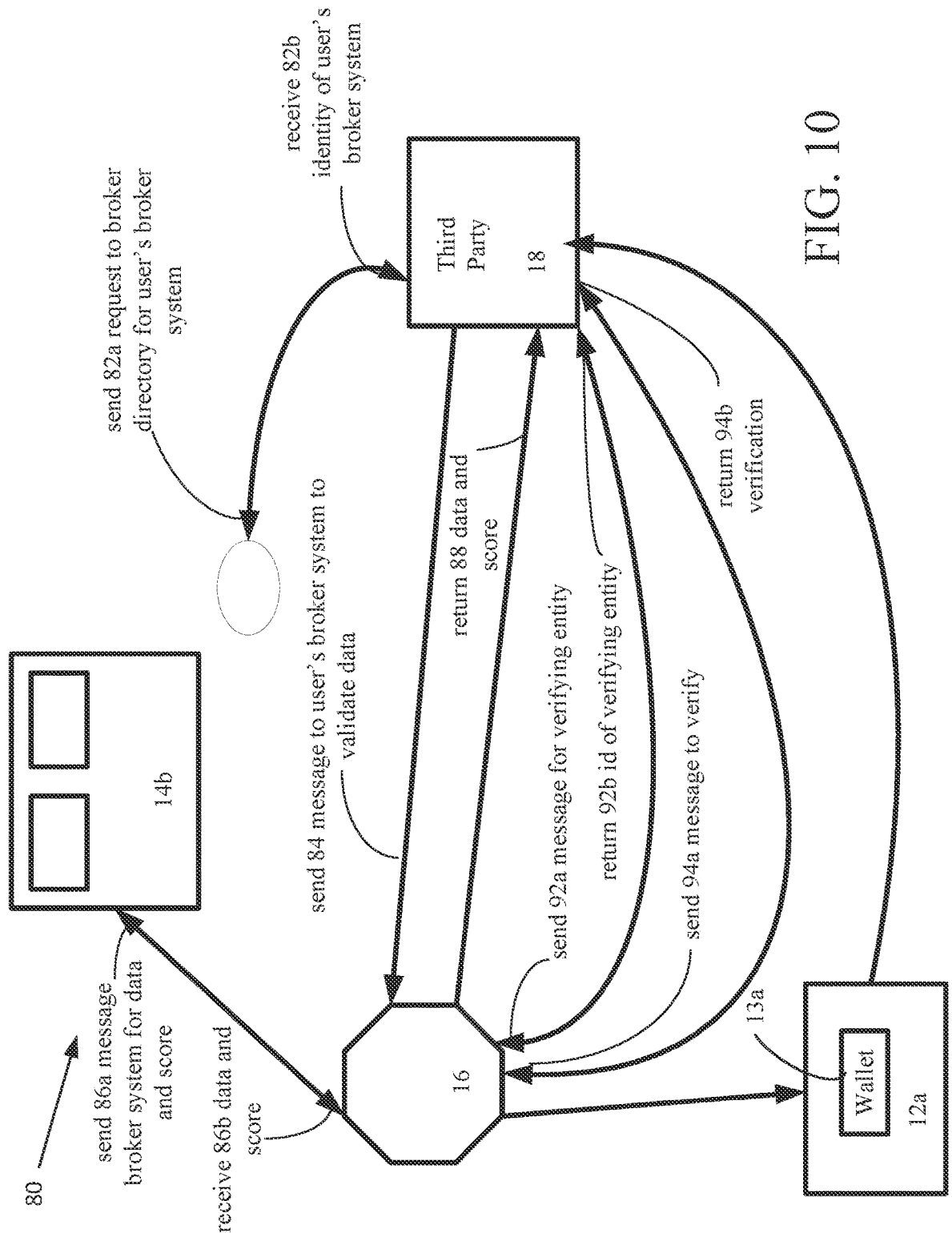

Referring now to FIG. 10, another process 80 is shown in which there is required validation of data through a private distributed ledger 14*b*. The third party system 18 sends 82*a* a message to a broker directory system 15 to locate the user's (potential driver's) broker system. The broker directory system 17 determines the user's broker system and sends 82b a message to the third party system 18, which includes the identity of the user's broker system. The third party system 18 sends 84 a message to the determined broker system 16, which is a request to the user's broker system 16 to validate data and return score data. There are many algorithms that could be used for scoring. For example, a simple algorithm may assign a score to an attestor as high, when the attestor is a governmental agency and may score an attestor as lower when the attestor is a personal contact. The user's broker system 16 validates data by sending 86a a message to the distributed ledger 14b for the data and the score (of the data or the attestor). The broker receives 86b from the distributed ledger 14b a message including the data and the score(s). The user's broker system 16 returns 88 the score(s) and status back to the third party system 18.

One approach for a private enterprise would be for an enterprise to define business rules that govern source attestor scores. The rules could be absolutes. Alternatively, over time the system that determines the score builds "a transactional footprint" for transactions, which is based on physical access points, logical access points, time of day, duration of use, etc. used with a transaction record. Initial algorithms are determined at the initial deployment, and then are refined based upon a regression pattern(s) that emerges.

Optionally, the third party system 18 requests 92a a lookup of the broker/owner for the party that verified the data. The third party receives 92b the address of the broker/owner that verifies the data. The broker/owner system that verifies the data signs the data with its digital signature. The broker/owner system sends 94a a message to the verifying broker/owner to verify a signature of the signed data. Upon receiving 94b a verification from the verifying broker/owner system, the third party system has verification of the data without actually having accessed the data. Optionally, the user can share 96 the data to be validated with the third party directly from the user's wallet.

Another process (not shown) can be used in which a third party requests validation of an attribute without actually disclosing the attribute. In this process the wallet 13a does not send a hash of the attribute, but allows a third party to request the verification of the attribute from the exchange. The rule is submitted to the exchange of the user (i.e. the request to validate if the user has a valid driver license and/or an absence of a criminal record or outstanding moving violations). The user would authorize the exchange for this rule to be processed. A trusted party attests to the valid driver license and/or the absence of a criminal record or outstanding moving violations.

Credential-Based Registration System

Described below are aspects of a mobile credential. The mobile credential is stored in a user's wallet 13a and is identified as authentic by use of the distributed ledger 14. The distributed ledger 14 is used to supply secure credentials to the user's wallet 13a all of which have been validated by the distributed ledger 14. The mobile credential is used to produce an access token that has a finite lifespan that is determined according to the estimate provided by the system of FIG. 4, and which can be adjusted. With the processes described below, the reader system can verify the access token as authentic and being from the user, and the user's wallet 13a can verify the vehicle as the vehicle to which the user should exchange credentials.

Figure 11:
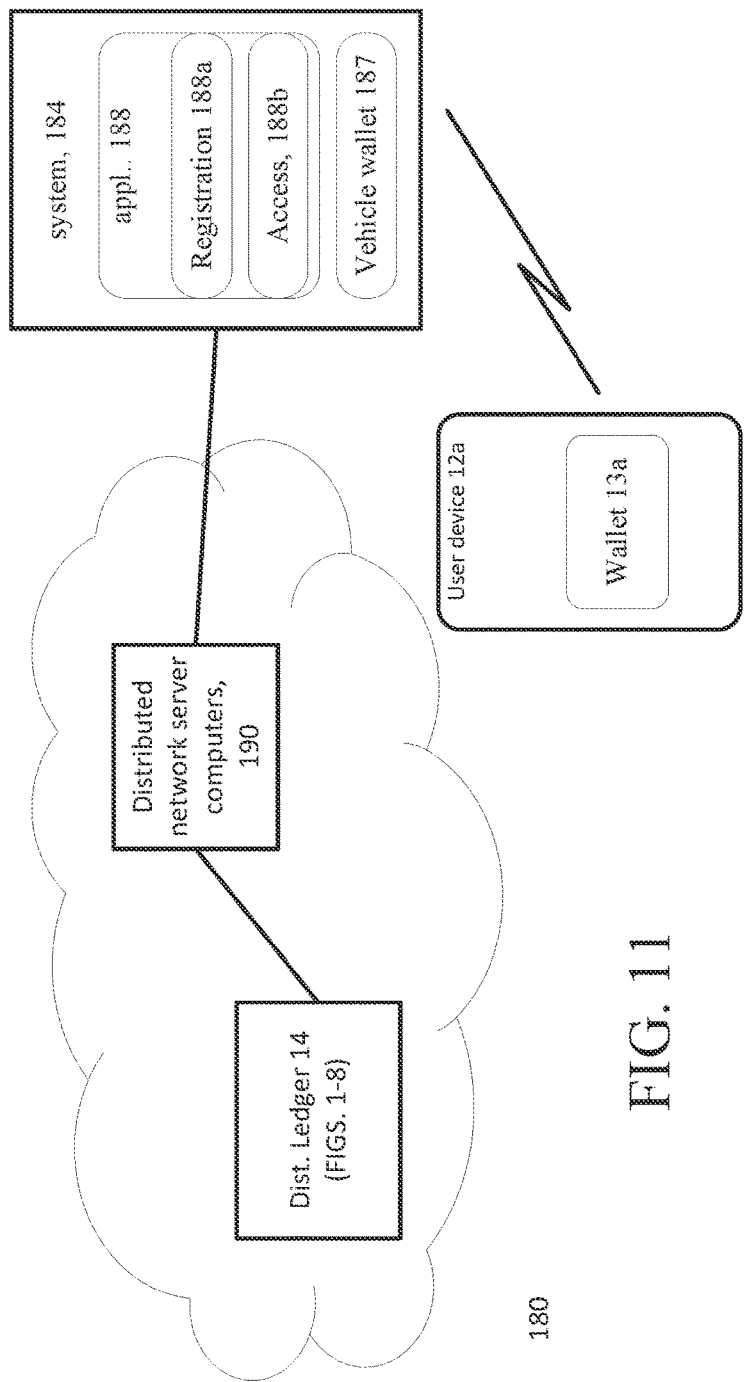
FIGS. 11 and 12 are block diagrams.

Referring now to FIG. 11, a credential-based registration/access system 180 that is a specialization of the system of FIG. 1, without the use of a broker system, is shown. The credential-based registration/access system 180 (registration/access system 180) is used for registration of a mobile credential with an access control system (not shown) using registration process 188a, the details of which will be discussed below. The registration/access system 180 includes the user device 12a having the wallet 13a. It is understood that a practical implementation would in general involve many such user devices/wallets of many users. The user device 12a and wallet 13a will be registered with the access control system and verified for use with the access control system. The registration allows a specific vehicle to be registered by the mobile credential.

The credential-based registration/access system 180 (system 180) also includes a vehicle system 184 including a vehicle wallet 187 and a vehicle application 188 that together with the user device 12a registers and verifies users, e.g., employees of an entity controlling the physical premises or logical structures, by use of the distributed ledger 14 and the distributed network server computers 190. The user device and the system can be any type of computing system, computing station, computer server, tablet device, etc., that includes Bluetooth® or other near field communication capabilities that can send out a beacon signal, as discussed below. The application 188 causes the system 184 to continually or periodically issue the beacon that is readable by the user device 12a to initiate a transaction with the system 184.

Figure 12:
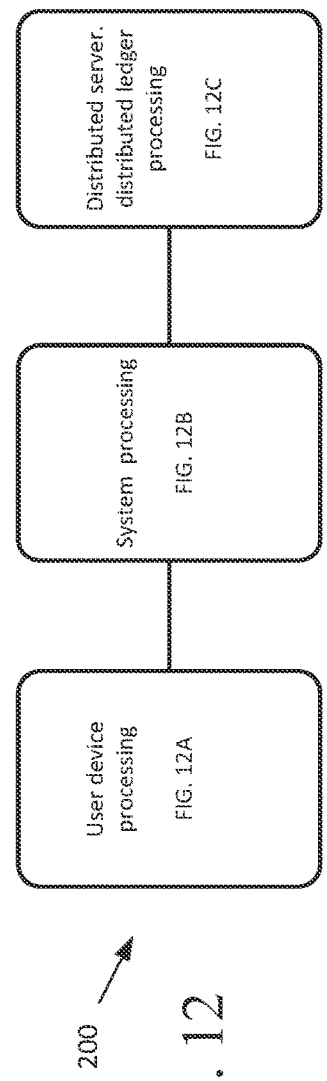

Referring now to FIG. 12, a credential-based registration process flow 200 for registration of a mobile credential stored on the user device 12a (more specifically in the wallet 13a) with access control systems is shown. Shown in FIG. 12, are user device processing (FIG. 12A), system processing (FIG. 12B) and distributed system/distributed ledger processing (12C). This credential-based registration process flow 200 (registration process 200) is shown for the user device 12a/wallet 13a, system 184/application 188, and the distributed servers 190 that interact with the distributed ledgers 14. The registration process 200 allows a user to verify a vehicle. The registration process flow 200 also allows the access control system to verify the identity of the user possessing the mobile credential for permitting registration for access to the vehicle. The described registration process 200 uses the application 188 to register and verify the user.

Figure 12A:
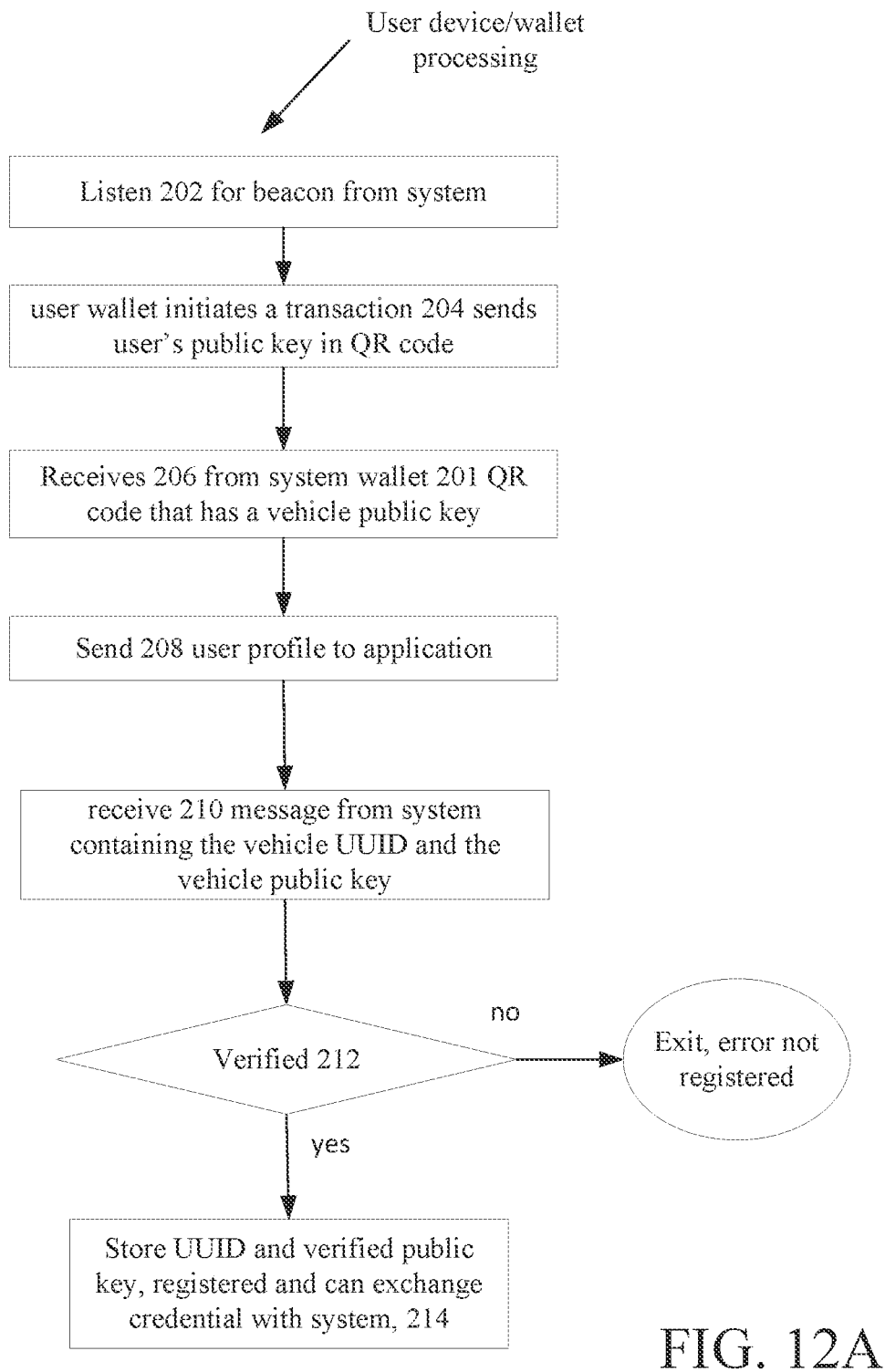
FIGS. 12A-12C and 13A-13C are flow diagrams.

Referring now to FIG. 12A, the user device 12a portion credential-based registration process flow 200 is shown. The user device 12a listens 202 for a beacon from the system. The beacon includes a message to cause the user's device to initiate 204 a transaction with the server to send the user's public key stored in the user's wallet 13a. The user's public key can be embedded in a code, such as a "QR"™ code (type of matrix barcode) that is stored in the user's wallet 13a. Other approaches could be used.

The user's wallet 13a requests 206 from a wallet 187 of the system 184, e.g., application 188, an access QR code has embedded therein a vehicle public key. In some implementations, the vehicle public key as well as a vehicle UUID (discussed below) are specific to a single physical vehicle. However, in other implementations, the vehicle public key as well as the vehicle UUID are specific to a plurality of vehicles of a single or related set of services. From the wallet 13a, a user profile corresponding the user associated with the device 12a is sent 208 to the application 188. As used herein a UUID is an identifier, e.g., such as a Universally Unique Identifier (UUID) per the UUID identifier standard that uses a 128-bit value.

Figure 12B:
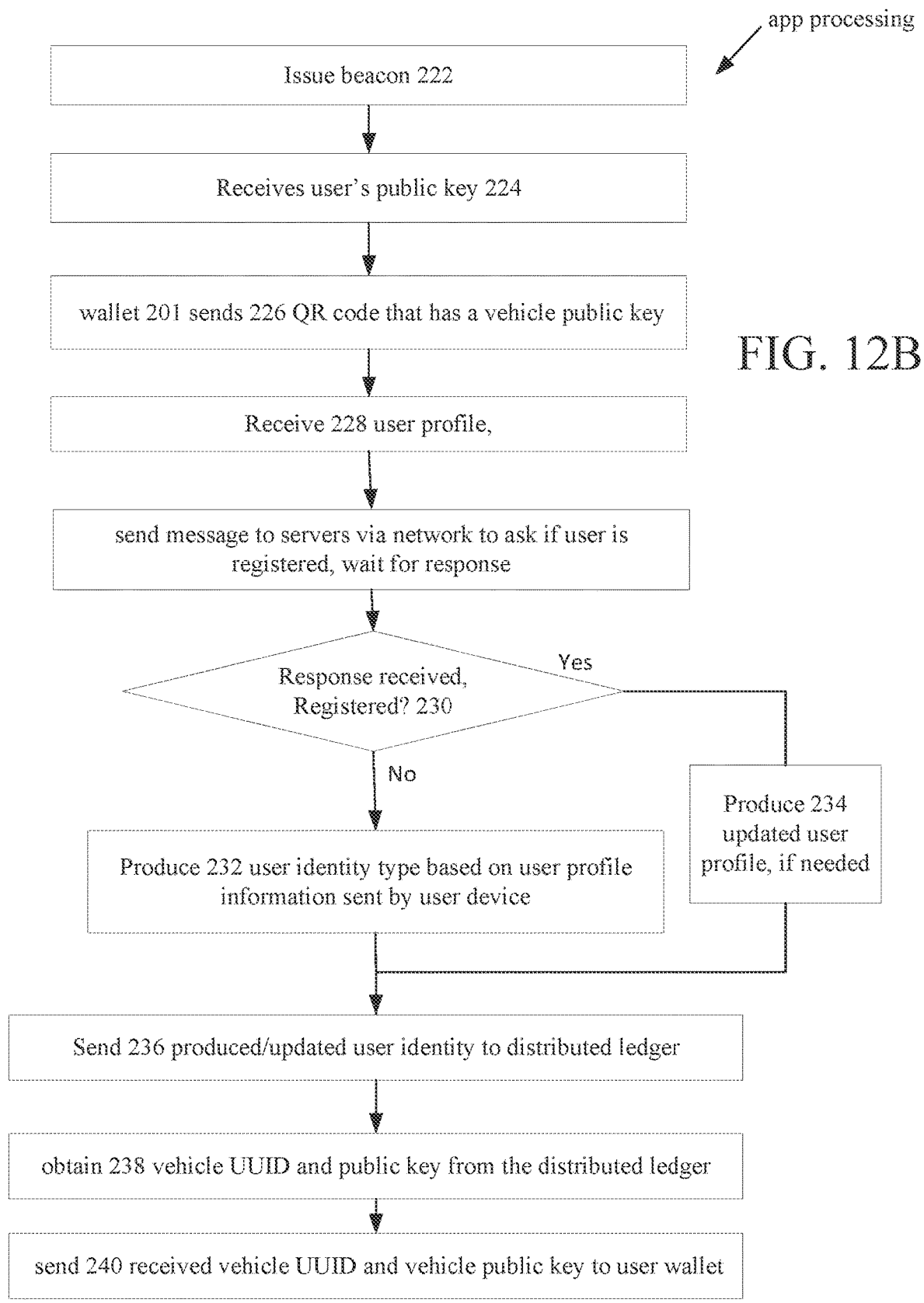

Referring now also to FIG. 12B, the application 188 causes the system to continually or periodically issue 222, a beacon, e.g., an electronic signal that is readable by the user device 12*a*. The application receives 224 the user's public key. A wallet 201 of the application sends 226 a QR code that has a vehicle public key. The application receives 228 the user's profile corresponding the user associated with the device 12*a*. Upon receiving the user profile, the application 188 sends 228 a message to distributed networked servers to search for the user via the distributed ledger 14. This search would be for the user's PII information.

Upon receipt 230 of a search result, if the user does not exist in the distributed ledger system 14, then the system will produce 232 a fault message. If the user profile does exist it may be updated 234, if needed, based on the received profile information. The system sends 236 updated user identity to the distributed ledger 14, along with the received public key to the distributed ledger system 14 where the profile, public key of the user are stored.

At this juncture, the user has been verified. Thus, upon verification of the user, the vehicle can be assured that it can exchange credentials with the user device 12*a* and wallet 13*a*. The system via the application 188 sends 238 a message to the distributed network servers to obtain the vehicle UUID and the vehicle public key from the distributed ledger 14 and upon receiving the vehicle UUID and vehicle public key, sends 220 the vehicle UUID and the vehicle public key to the wallet 13*a* for verification and storage. The wallet 13*a* receives 210 a message from the system, which contains the vehicle UUID and the vehicle public key. The wallet 13*a* verifies 212 the vehicle public key using similar processes as discussed above. If verified the user device 12*a* and wallet 13*a* can be assured that this is a vehicle for which the user device 12*a* and wallet 13*a* can furnish a mobile credential. When verified the wallet stores 214 the UUID and vehicle public key.

Figure 12C:
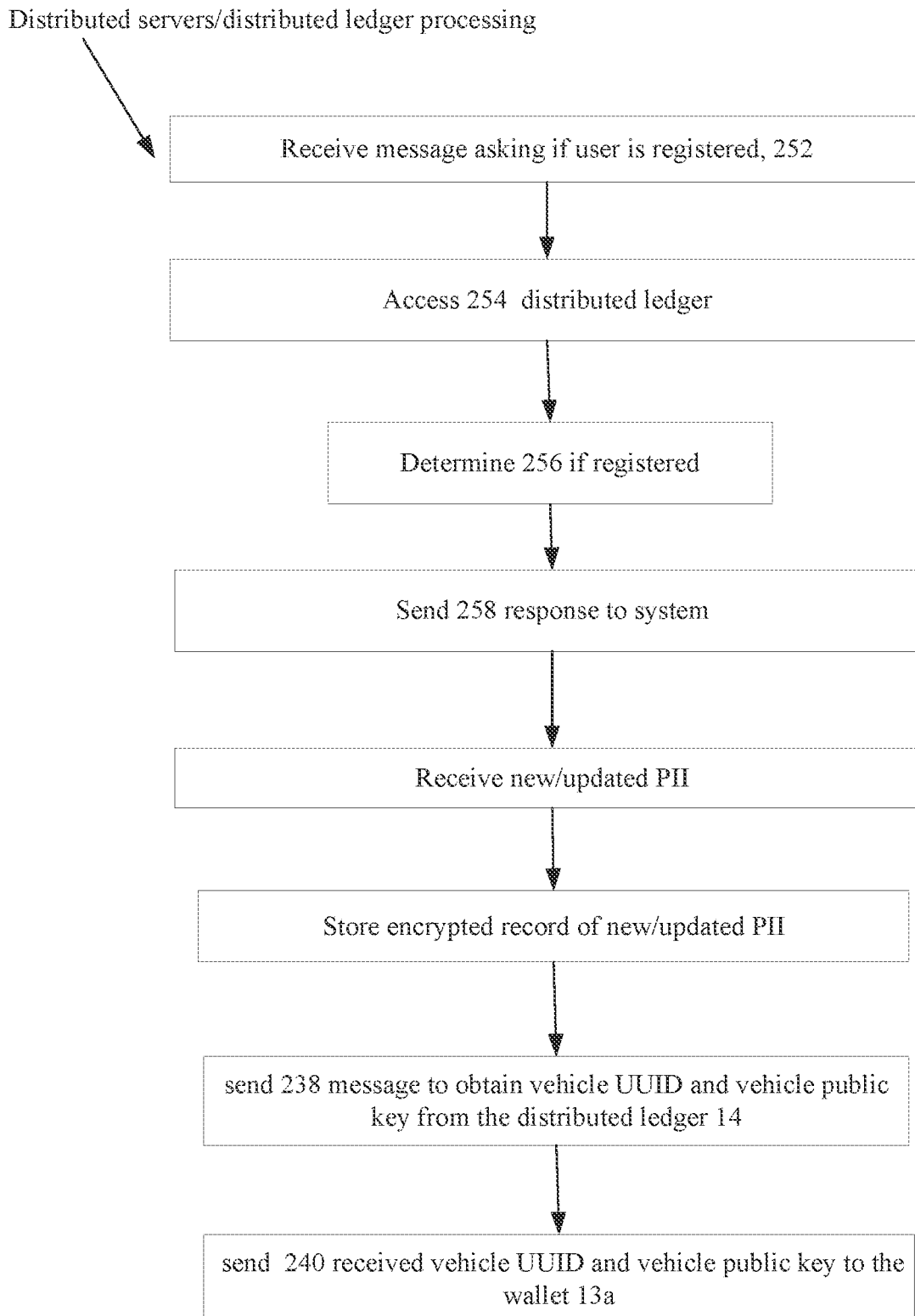

Referring now to FIG. 12C, the distributed servers receive 252 a message from the system to conduct a search for a profile of the user. The distributed servers access 254 the distributed ledger 14. The distributed servers determine 256 if a profile exists by searching the distributed ledger system 14 for a profile of the user. The distributed servers send 258 a result of the search, e.g., registered, not registered, expired registration, etc. to the system 18.

Credential-Based User Access

Credential-based access processing for permitting access using a registered mobile credential stored on the user device 12*a* (more specifically in the wallet 13*a*) to an access control system, uses the user device, access systems and the distributed system/distributed ledger system. Access processing allows a user, e.g., user, to verify a vehicle and vice-versa.

The credential process uses a credential exchange mechanism that allows a user's wallet 13*a* to verify the vehicle, obviating need for a central, certificate issuing authority, by each vehicle having a unique certificate similar to those commonly found today in website certificates. However, in this instance, the company is the issuer of the certificate. This gives the ability to have the credential carrier roles and permissions, conveyed by the reader application exchanging the roles and permissions of a user, without having to go back to a central service. This allows local control (exchange process of certificates). The mobile wallet 13*a* can access permissions from a central facility (one time load) without the local control having to go back to the central facility each time access is attempted.

User access to a vehicle can give door access to the vehicle, if the user has a seal (discussed below) and is scheduled for access to the vehicle (e.g., rental). As used herein, a "seal" is a token that is registered on a user' wallet 13*s* to verify that the user has gone through an initial authentication process. This "seal" would contain a signature from the server 184 that validated the user's wallet under specified conditions (time interval, level, etc.).

The user is registered and when the user shows up at the vehicle, the user will scan an outside reader or the vehicle will sense credentials to gain access. Details of these processes are discussed below.

Digital certificates are issued by a certificate authority or certification authority (CA), i.e., an entity that issues and certifies digital certificates, which certification is used to verify the ownership of a public key by the named entity associated with the certificate. The certification enables others that rely upon signatures or assertions made about the private key as corresponding to the certified public key. In this model of trust relationships, a CA could be a third party or in some implementations could be the entity itself rather than a trusted third party—trusted both by the owner of the certificate and by parties that would be relying on the certificate. Public-key infrastructure (PKI) schemes feature certifying authorities.

Described is a vehicle application 188 to access and verify users or other service providers. The user's device 12*a* listens for a beacon. The vehicle broadcasts a beacon (ID) that the user's device, e.g., smartphone receives and, which the mobile wallet 13*a* detects. The user device 12*a* connects to the vehicle computer, and the wallet 13*a* via the device 12*a* requests that the computer provide its credentials to the user device 12*a*. The beacon includes a message to cause the user's device 12*a* to initiate 604 a transaction with the application on the computer. The user's wallet 13*a* requests 606 a vehicle certificate, OCSP and vehicle UUID (discussed below).

The user's device 12*a* verifies 608 the credentials sent to the wallet 13*a* from the vehicle wallet 201, e.g., the vehicle certificate, the OCSP and the vehicle UUID. If valid, then the system will provide its UUID, the vehicle certificate (public key for the vehicle) and company certificate (e.g., public key of the rental company). The wallet 13*a* verifies if, the wallet 13*a*, is paired with the rental company.

Since the mobile wallet knows the company's public key, the mobile wallet can trust that any packets signed by the company are valid and can be trusted. When the mobile wallet 13*a* accesses a vehicle, the vehicle provides its specific public key to the mobile device 12*a* (wallet 13*a*). Authenticity of the vehicle is determined by the wallet 13*a* through verification 608 of the vehicle's certificate. The verification process has the wallet 13*a* determine whether the vehicle certificate was signed by the company. If the certificate was signed by the company, then the wallet 13*a* verifies that the vehicle certificate and the signature match because the wallet has the company's public key and the wallet can verify the signature. If the signature is valid, then the wallet 13*a* knows that the vehicle certificate is authentic.

Although the certificate is authentic the wallet needs to verify that the certificate has not been revoked. The wallet can do this verification a number of ways.

Upon, the user's wallet 13*a* verifying the vehicle credentials, e.g., vehicle certificate, a revocation status and vehicle UUID, the user's wallet sends 610 a JWT message to the door kiosk app. The JWT message follows the so called JSON Web Token (JWT) format that is a JSON-based open standard (RFC 7519) for producing tokens that assert some number of "claims." The generated tokens, as above, are signed by the token producer's private key, so that door app in possession of the producer's public key is able to verify that the token is legitimate. An exemplary JWT message is

| JWT Format | |
|---|---|
| Claims | |
| iss | Issuer. The UUID of the Mobile Wallet |
| aud | The UUID of the Reader being accessed |
| exp | Expiration time of the token. Set to 30 seconds |
| jti | Unique token id. Server will track IDs over the expiration time period to ensure not duplicate JWT calls are made |
| iat | Time the token was issued/created |

The JWT contains the "iss" attribute which is a unique ID for the wallet. This unique ID is used by the reader or other system to obtain the stored public key and the JWT can be verified. If the token is not valid then an error response is sent to the wallet and access is not provided. The JWT has an "aud" attribute that identifies the destination of the token (i.e., the reader UUID). The JWT also includes an "exp" attribute that sets the expiration time of the token, and a "jti" attribute, i.e., and ID that can be used by the Reader or which can be used by an upstream system to ensure that the token can be used only once during the validity time (i.e., replays would be prevented). The "iat" attribute indicates the time that the JWT was issued.

Thus, the application 188 can send to the user device containing the wallet 13a a verified access or access error depending on the outcome of the process. All exchanges are logged in the distributed ledger for audit tracking, etc.

The JWT can also contain access policies that the reader can implement locally. For example, the JWT could contain roles that the wallet belongs to and those roles can be used by the reader to determine if the access should be provided or not with all decisions being made by the reader unit. This provides reduced latency in comparison with a centralized system approach where decisions based on roles, etc. are centrally made. The roles and access policies would be part of a JWT payload. A requirement would thus be that those roles and policies would need to be signed by the company and preferably would have an expiration date.

The reader will trust those policies if they meet the validation criteria which is composed of the follow types of checks:

The policies contain the wallet ID
The policies are signed by the Company
The policies are not expired The specifics of the encoding of the JWT payload have not been provided. However, the payload could be a binary payload inside of the JWT, an encoded attribute, or could be a second JWT produced by the company that the mobile wallet provides in addition to its own JWT, i.e., the company provided JWT for access. This second JWT produced by the company would contains the access policies, wallet id, and expiration time, would be signed by the company and the "iss" of the company.

Figure 13A:
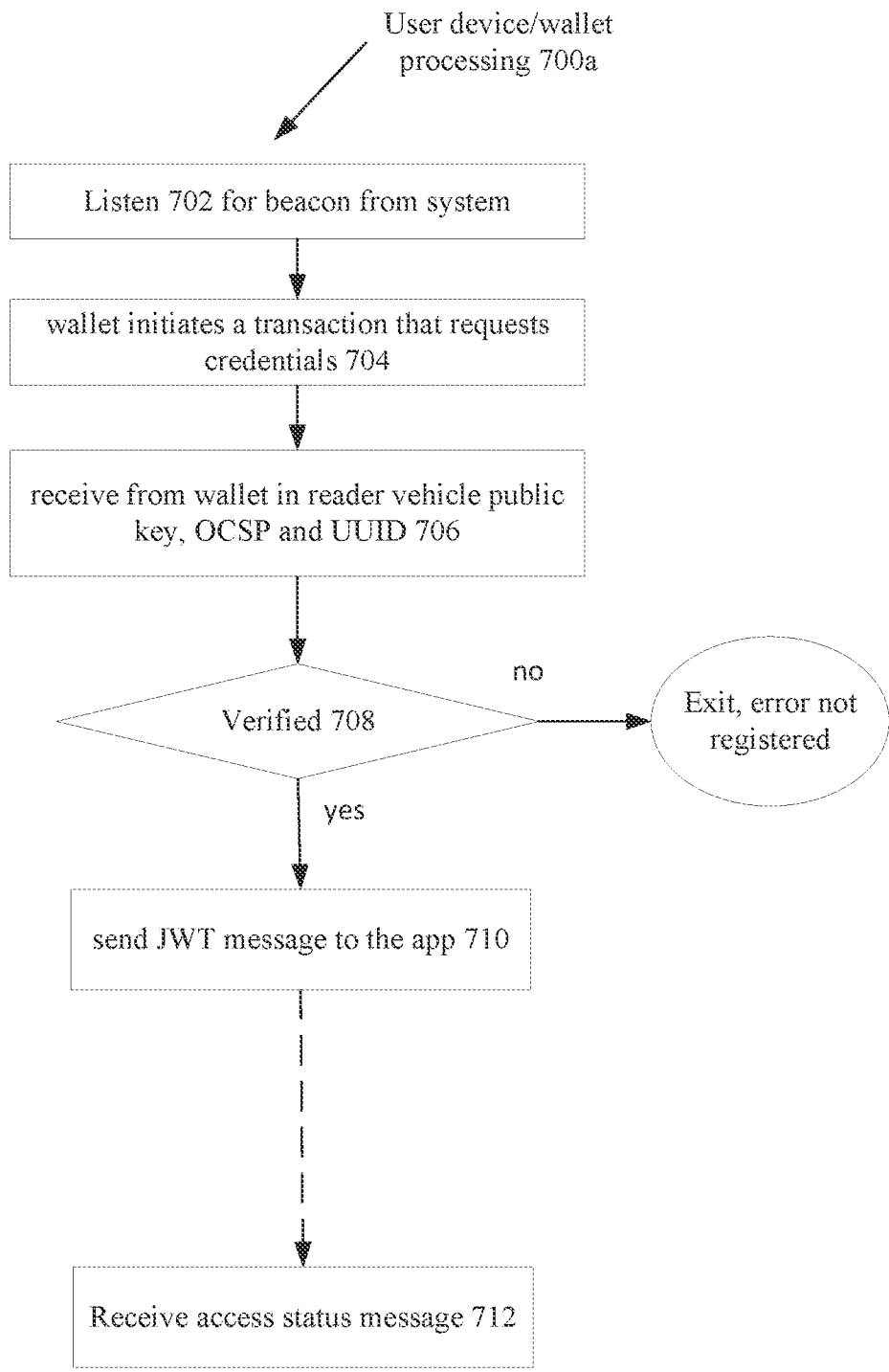

Referring now to FIG. 13A, the user device 12a portion 700a of the credential-based access process 700 is shown. The user device 12a listens 702 for a beacon from a reader. The reader broadcasts a beacon (ID) that the smartphone receives and, which the mobile wallet detects. The user device 12a connects to the reader, and the wallet 13a via the device 12a requests that the reader provide its credentials to the user's device 12a. The beacon includes a message to cause the user's device 12a to initiate 704 a transaction with the reader to connect with the application on the reader. The user's wallet 13a requests 706 from a wallet 701 in the reader, e.g., application 188, a vehicle certificate, OCSP and vehicle UUID (discussed below).

The user's device 12a verifies 708 the credentials sent to the wallet 13a from the wallet 701 of the system 184, e.g., the vehicle certificate, the OCSP and the vehicle UUID. If the reader is valid, then the reader will provide its vehicle UUID, the vehicle certificate (public key for the vehicle) as well as the company UUID and company certificate (public key of the company). The wallet 13a verifies if, the wallet 13a, is paired with the correct vehicle.

Other approaches include the beacon ID being that of the company UUID and if the wallet 13a is paired with that company, the wallet 13a (via the device 12a) then connects to the system and requests details. The wallet 13a via the device 12a either connects and determines if the beacon is from a valid system or the beacon ID itself is formatted such that beacon from a valid system informs the wallet 13a that the beacon is from the reader and the wallet verifies the specifics by connecting to the reader.

The user's wallet connects to the application once the beacon is detected. The application has the vehicle certificate, the vehicle UUID, and a revocation status, e.g., such as via the "Online Certificate Status Protocol" (OCSP) as discussed above. Other approaches could be used.

Since the mobile wallet knows the company's public key, the mobile wallet can trust that any packets signed by the company are valid and can be trusted. When the mobile wallet 13a accesses the reader, the reader provides its vehicle specific public key to the mobile device 12a (wallet 13a). The mobile wallet 13a does not know if this vehicle is authentic and part of the company that the wallet 13a holds a mobile credential for, and thus before the wallet 13a exchanges its credentials, the wallet 13a needs to verify for certain that the reader is authentic.

Authenticity of the reader is determined by the wallet 13a through verification 708 of the vehicle's certificate. The verification process has the wallet 13a determine whether the vehicle certificate was signed by the company. If the certificate was signed by the company, then the wallet 13a verifies that the vehicle certificate and the signature match because the wallet has the company's public key and the wallet can verify the signature. If the signature is valid, then the wallet 13a knows that the vehicle certificate is authentic.

Although the certificate is authentic the wallet needs to verify that the certificate has not been revoked. The wallet can do this verification a number of ways as discussed above, e.g. directly through an OCSP request or with an OCSP response (i.e. OCSP stapling), as discussed above, or CRL.

Upon, the user's wallet 13a verifying the vehicle credentials, e.g., vehicle certificate, a revocation status and vehicle UUID, the user's wallet sends 710 a JWT message to the reader. The JWT message follows the so called JSON Web Token (JWT) format discussed above. The generated tokens, as above, are signed by the token producer's private key, so that door kiosk app in possession of the producer's public key is able to verify that the token is legitimate. The claims are used to pass identity of authenticated users between an identity provider and a service provider. The tokens can be authenticated and encrypted. Upon verification of the JWT message by the servers, the servers cause the reader to send an access status message that is received 712 by the wallet 13a, allowing or denying access.

Figure 13B:
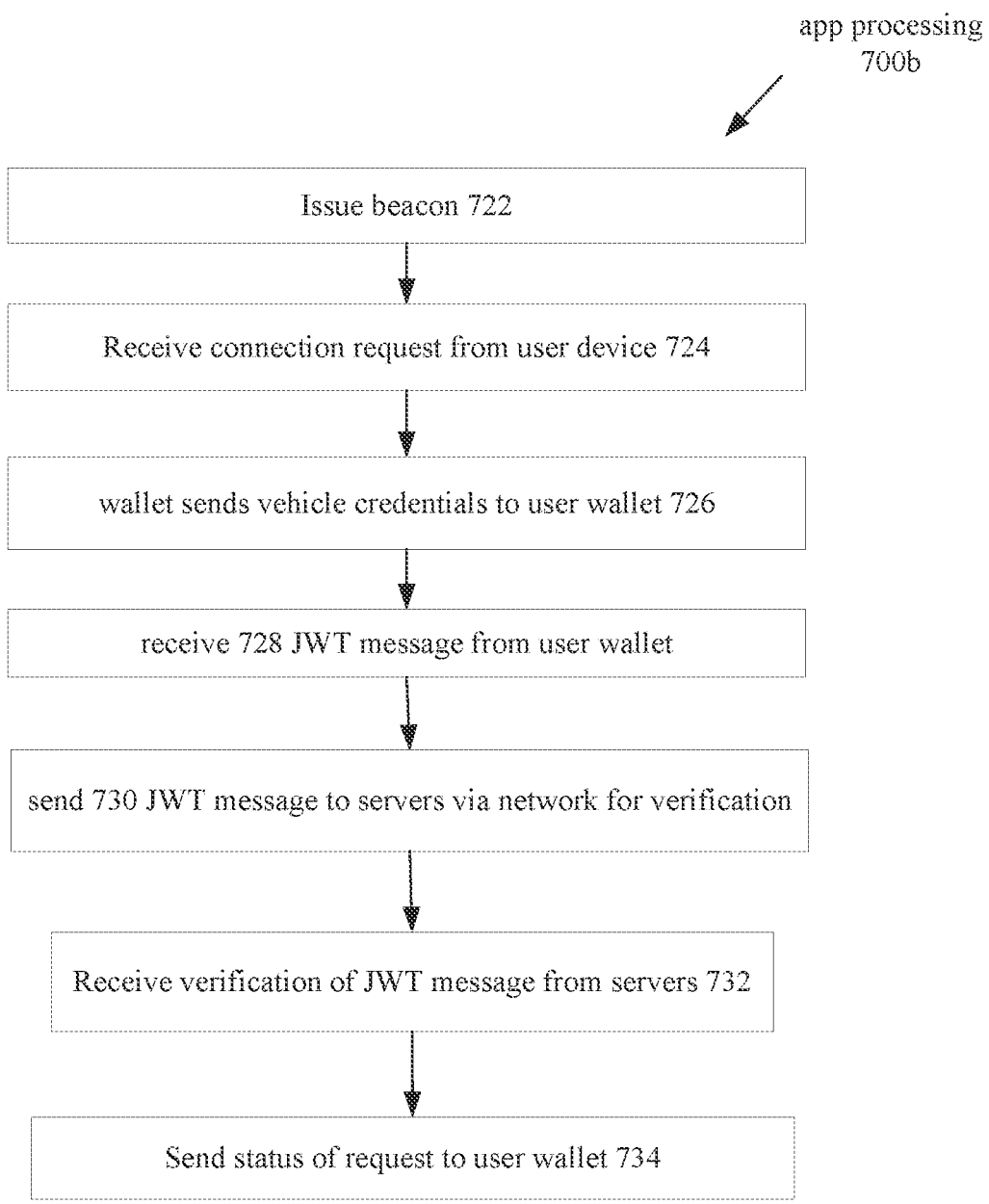

Referring now also to FIG. 13B, the application 188 processing 700b causes the system reader to continually or periodically issue 722, the beacon that is readable by the user device 12a and which causes the user device to request 724 a connection to the reader. As mentioned above, the user device 12a upon connecting to the reader has the reader provide 726 its credentials to the user's device 12a (wallet 13a). If the verification by the wallet was successful, the wallet sends the JWT message, and upon receipt 728 of the JWT message by the reader, the JWT is sent 730 to the distributed network to a server that is used to verify the JWT token. Upon verification of the JWT message by the servers, the servers send the reader an access status message that is received 732 and is sent 734 to the wallet 13a allowing or denying access to the vehicle.

Figure 13C:
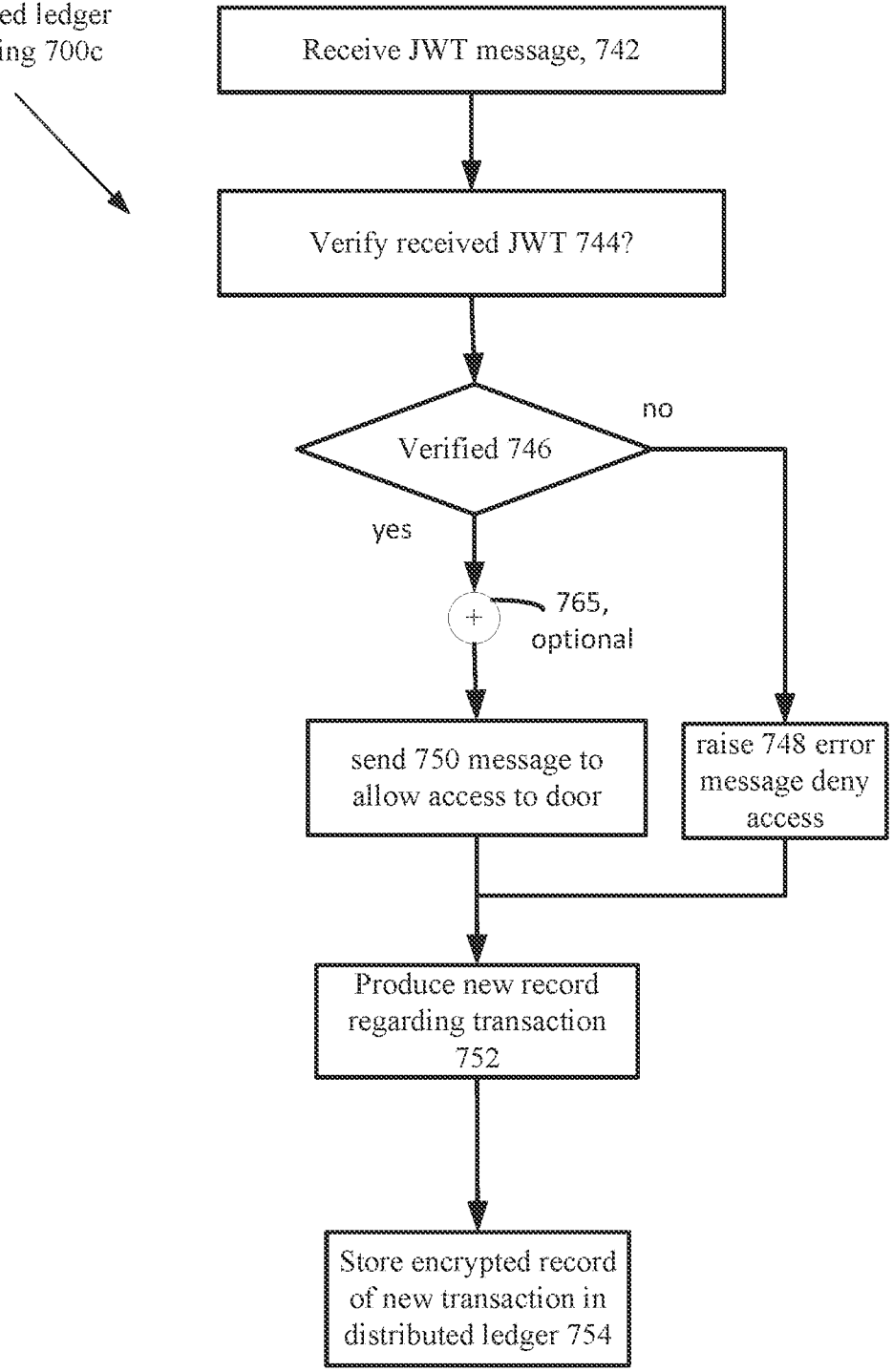

Referring now also to FIG. 13C, the distributed servers/distributed ledger processing 700c is shown. The JWT is received 742 by the distributed servers and is verified 744. If the JWT is not verified, an error is raised 748 (see below). If the JWT is verified, 746 the user is granted access 750, and an access control system grants the access and sends signal to unlock a door, etc. In addition, whether the JWT is verified or not verified, a corresponding entry record of either an access entry or an access denied entry is produced 752 as an access log that is stored 754 and maintained in the distributed ledger system.

All exchanges are logged in the distributed ledger for audit tracking, etc. Records are added to the distributed ledger as transactions and include a hashed record of the transaction, what was exchanged, the signatures of the parties, and may include additional detailed information depending on the type of distributed ledger used. The information stored for audit can include the date and time that the mobile wallet sent a JWT, the JWT parameters, and the access status or error conditions.

Access Validation Using Distributed Ledger Identity Management

FIG. 13 depicts a access validation system 1400. The access validation system 1400 can incorporate features of and perform various processes described herein, including but not limited to the system 10 and the use of the distributed ledger 14 of the system 10 to securely authenticate identity information regarding users without revealing PII of the users. The access validation system 1400 can validate users for access to spaces, such as buildings, based on particular conditions that can involve the PII of the users. For example, access to a space may be restricted based on a policy that includes rules for users to have been verified for having immunity to or been treated for or vaccinated for a medical condition, such as a disease or infection (e.g., bacterial infection, viral infection). The access validation system 1400 can enable such policies to be implemented by enabling users (e.g., using a user device) to provide a credential that indicates a medical status of the user, is verifiable to have been attested to by a trusted source, has not expired, and does not require output of PII other than the status of the user. The access validation system 1400 can be used in various applications, including but not limited to public spaces (e.g., transportation centers, theaters, stores, medical facilities, restaurants, arenas, garages, coffee shops, among others) in which the user and an administrator of the public space may not have a predefined relationship, as well as semi-private or private spaces (e.g., office buildings, such as to interface with an environmental health and safety (EHS) department, human resources department, or compliance department of an organization that operates a building).

Implementing the access validation system 1400 can enable real-time identification, isolation, and contact tracing regarding the medical statuses of users without outputting of PII other than the statuses of the users. The access validation system 1400 can enable the user to provide instructions to opt into or opt out of such operations, and anonymity of the end users can be preserved (e.g., the medical status can be associated with an anonymous identifier of the user, such as a hash of an identifier of the user used by the distributed ledger 14).

The access validation system 1400 can include the user device 12a, which can operate the wallet 13a. The wallet 13a can include a credential 1404 regarding a user of the user device 12a. The user can be a person, an organization (e.g., a group of people to which the credential 1404 applies), or an object. The credential 1404 can be an identity of the user, such as an immunity identity.

The credential 1404 can include a value representative of an attribute of the user. The credential 1404 can include a value that indicates the medical status of the user or a policy associated with the medical status. For example, the credential 1404 can have a first value that indicates that the user complies with the policy (e.g., the user has immunity to, been treated for, or been vaccinated for the medical condition), or a second value that indicates that the user does not comply with the policy (e.g., the user does not have immunity to or has not been tested for, has not been treated for, or has not been vaccinated for the medical condition).

The wallet 13a can present the value of the credential 1404, such as for validation by external systems 18. The wallet 13a can present the value of the credential 1404 using an output device of the user device 12a, such as at least one of a display device and an audio output device. For example, the wallet 13a can present the value of the credential 1404 to include at least one of a visual representation of the value (e.g., color such as green for the first value and red for the second value, text) and audio representation of the value (e.g., audible word representative of the value). The wallet 13a can present the value of the credential 1404 using a QR code. The wallet 13a can be a physical representation of the credential 1404, such as a printed indication, such as a printed QR code.

The access validation system 1400 can include one or more external systems 18. The external system 18 can include an access controller 1408 that selectively controls movement into or out of the space responsive to validation of access information, such as validation of the credential 1404. The external system 18 can include or be associated with image- and non-image-based systems that monitor movement into and out of the space. The access controller 1408 can perform access control by controlling operation of doors, locks, turnstiles, or other devices that restrict movement into or out of the space.

The access controller 1408 can perform the access control responsive to receiving a manual input indicative of validation of the credential 1404 (e.g., based on an administrator reviewing and validating the credential 1404 and providing a command to the access controller 1408). The access controller 1408 can include a device such as an image capture device, card reader, or RFID detector, among others, that can receive the credential 1404, enabling the access controller 1408 to perform access control responsive to the credential 1404. The access controller 1408 can transmit a request signal to the user device 12a to request the user device 12a to output the credential 1404 from the wallet 13a, such as to present the credential 1404 or transmit the credential 1404 for reception by the access controller 1408.

The access validation system 1400 can include the distributed ledger 14. The distributed ledger 14 can maintain a record 1412, which can incorporate features of the record 40 described with reference to FIG. 5. The record 1412 can include information representative of at least a portion of a health record of the user associated with the record 1412. The record 1412 can include at least one hash (or hashed pointer to) at least one attribute of the health record. The record 1412 can be a data structure that includes one or more data entries that include an attribute type of the attribute, a hashed and encrypted value of the attribute, an attestor signature of the hashed and encrypted value of the attribute, and an address of the attestor. For example, the attribute of a data entry can be a medical status, such as a pass status (e.g., first value) indicating that the user is immune to or has been treated for or vaccinated for the medical condition, or a fail status (e.g., second value) indicating that user is not immune to, has not been treated for, or has not been vaccinated for the medical condition. An example of the record 1412 is set forth below.

| User Attribute | Hashed and Encrypted Value | Attestor Signature | Attestor Address |
| --- | --- | --- | --- |
| Name | encrypt(Name) | Signature of encrypt(Name) | attst@medicalassociates.org |
| Date of Birth | encrypt(Date of Birth) | Signature of encrypt(Date of Birth) | attst@medicalassociates.org |
| Medical Status | encrypt(Pass) | Signature of encrypt(Pass) | attst@medicalassociates.org |

The distributed ledger 14 can maintain and update the record 1412 using data received from an attestor system 1416. The attestor system 1416 can include a computer, such as a server operating a health record database, which maintains health record data and is operated by an entity that can be a trusted source of information regarding the medical status. For example, the entity can be a healthcare provider or a government agency. The attestor system 1416 can receive health record data from an attestor, such as a medical professional or government official. The attestor system 1416 can include or communicate with one or more client devices (not shown) by which the attestor can provide and attest to the health record data. While FIG. 13 depicts the attestor system 1416 as a separate component from the distributed ledger 14, the attestor system 1416 may include or maintain one or more portions of the distributed ledger 14 (e.g., the attestor system 1416 can include at least one of the distributed databases 32a-32n and computers 36a-36n described with reference to FIG. 5). The distributed ledger 14 can periodically request the health record data from the attestor system 1416. The attestor system 1416 can periodically transmit the health record data to the distributed ledger 14, such as to perform periodic updates of the distributed ledger 14. The distributed ledger 14 can request the health record data responsive to a request from the wallet 13a to receive or update the credential 1404.

The distributed ledger 14 can receive the health record data, such as the medical status, based on information provided by the attestor. For example, the attestor can indicate that the user has been tested for the medical condition and found to be immune, has been treated for the medical condition, or has been vaccinated for the medical condition, using attestor system 1416. The distributed ledger 14 can update the record 1412 responsive to the user device 12a requesting the credential data, such as to assign a time stamp to the record 1412 indicating a most recent time at which the status of the user was determined to be the first value and outputted as the first value.

By using the distributed ledger 14 to encrypt the medical status, the access validation system 1400 can enable the medical status to be outputted without outputting other PII of the user, such as the date of birth of the user, or whether the medical status was determined for the user by testing for immunity, treatment, or vaccination (e.g., the distributed ledger 14 can abstract details regarding how the medical status was determined to a level of pass or fail regarding the medical condition). As such, the access controller 1408 can verify the medical status without having accessed the data maintained in the health record of the user.

The wallet 13a can generate or update the credential 1404 using credential data received from the distributed ledger 14. The credential data can include a representation of the medical status stored in the record 1412.

The user device 12a (e.g., by operating an application) can receive the credential data, such as by transmitting a request to the distributed ledger 14 for the credential data. The user device 12a can generate the request for the credential data by signing the request with a signature or key that the distributed ledger 14 can verify in order to identify the record 1412 from which to provide the credential data. The user device 12a can generate the request for the credential data responsive to a request for the credential data received from the external system 18, or responsive to user input (e.g., user input received via a user interface of the user device 12a implemented by the application). The user device 12a can use the service broker system 16 as described, for example, with respect to FIGS. 1 and 6, to retrieve the credential data from the distributed ledger 14.

The external system 18 (e.g., access controller 1408) may request the credential data from the distributed ledger 14 (e.g., rather than relying on the user device 12a as in intermediary device) and perform the access control using the received credential data. For example, the external system 18 can transmit a request to the distributed ledger 14 that is signed using a signature or key associated with the user (or associated with the entity that operates the external system 18, such as if the entity that operates the external system 18 is trusted by the entity that operates the distributed ledger 14 or the attestor system 1416).

Figure 14:
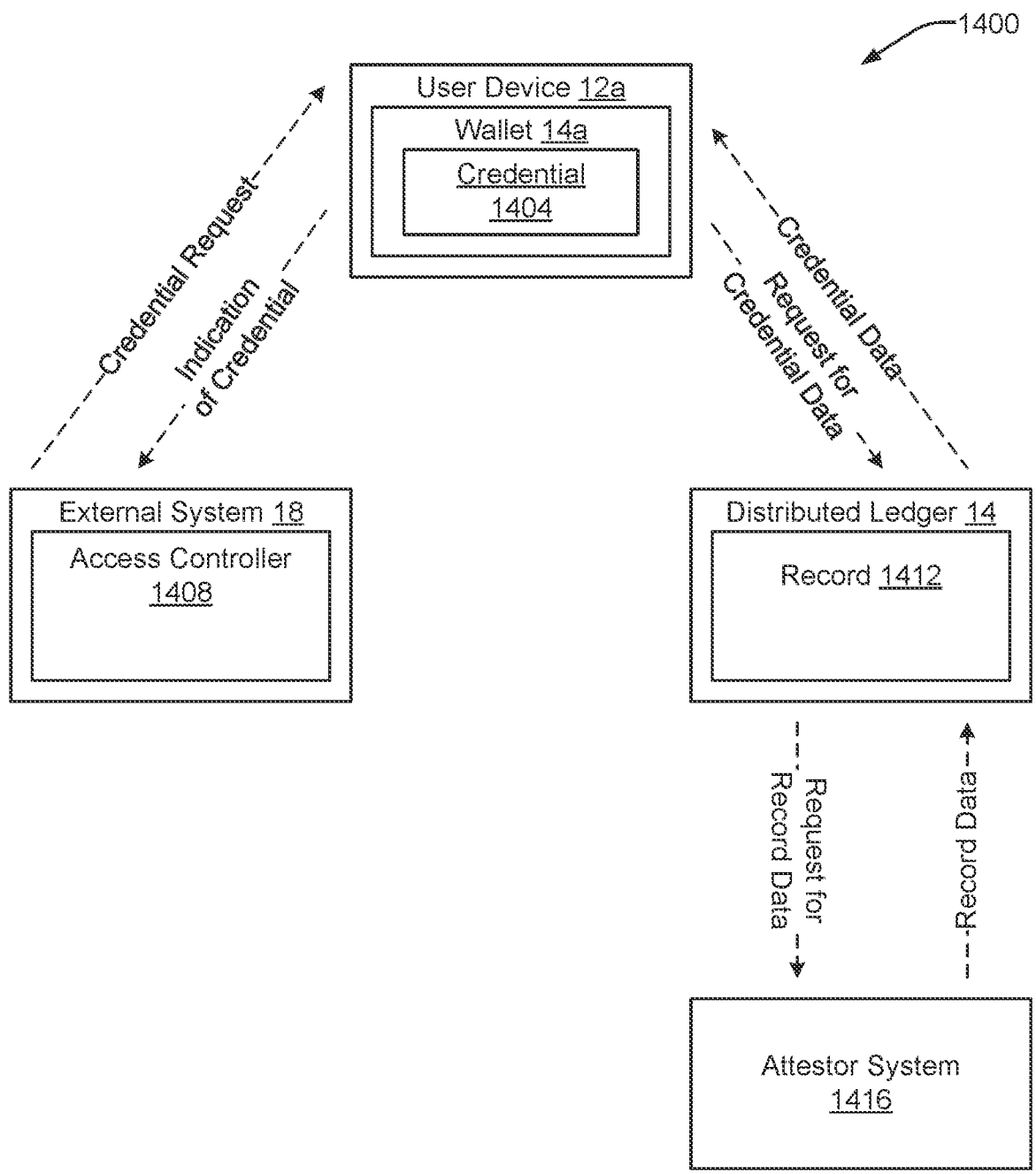
FIG. 14 is a block diagram of an access validation system.
Figure 15:
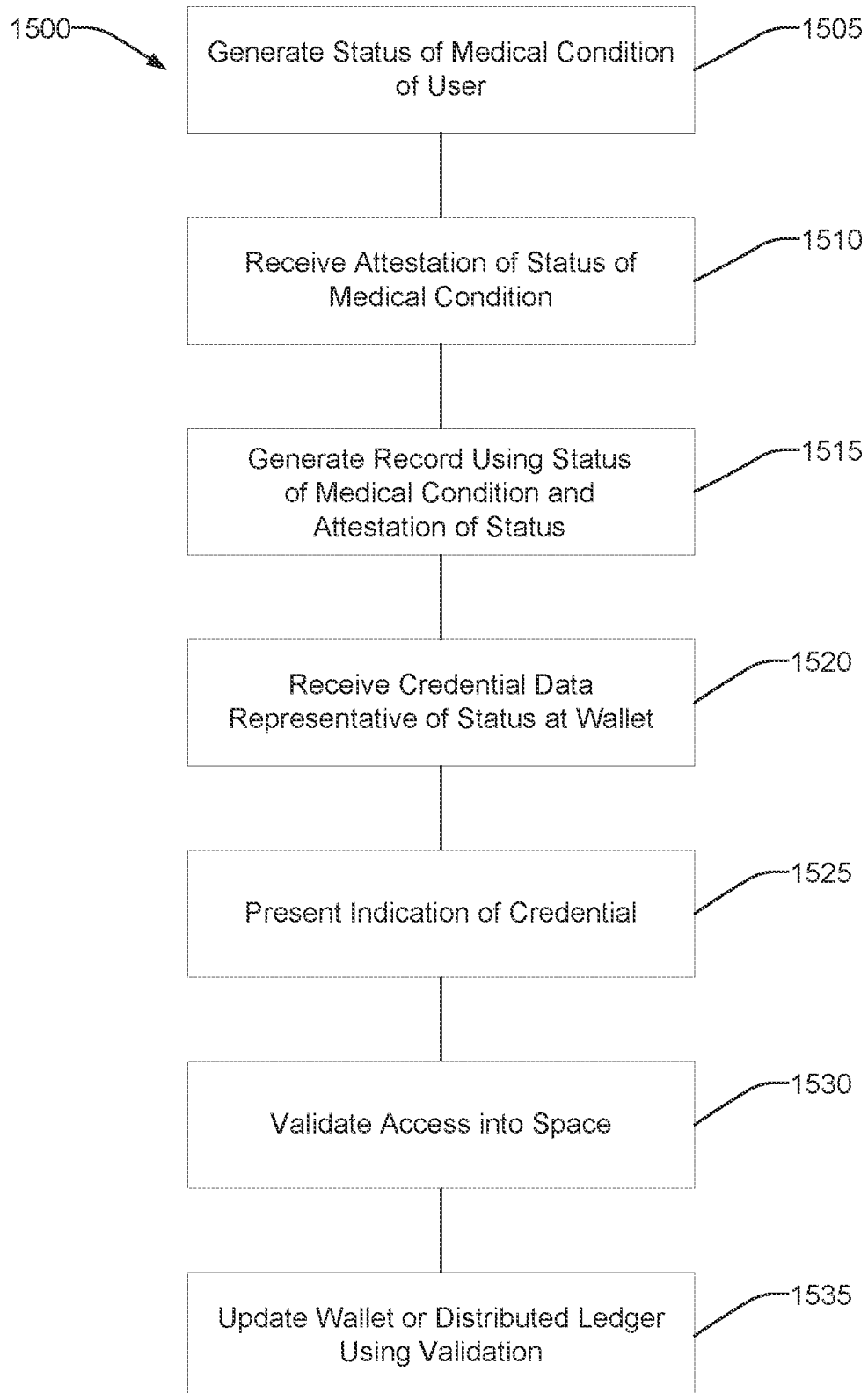
FIG. 15 is a flow diagram of a method of access validation using distributed ledger identity management.

FIG. 14 depicts a method 1500 of access validation using distributed ledger identity management. The method 1500 can be performed using the access validation system 1400 or various components thereof. The method 1500 can be performed to validate access into a space, such as a building, for a user.

At 1505, a medical status regarding the user is generated. The status can be generated using input from regarding a test, treatment, or vaccination performed for the medical condition. For example, the status can be generated by a health record system operated by a medical office or medical professional that determines the medical status. The status can be generated to have a first value that indicates that the user has been found (e.g., by testing) to be immune for the medical condition, to have been treated for the medical condition, or to have been vaccinated for the medical condition. The status can be generated to have a second value that indicates that the user has not been found to be immune to the medical condition, has not been treated for the medical condition, and has not been vaccinated for the medical condition. The medical status can be generated in and maintained in a health record database.

At 1510, an attestation of the medical status is received. The status can be attested to responsive to user input received from one or more entities. For example, an application can authenticate the identity of an administrator, such as at least one of a medical professional and a government official, that is trusted to perform the attestation or associated with an entity (e.g., organization) that is trusted to perform the attestation. The application can receive input indicating attestation to the medical status, such as a signature of the administrator.

At 1515, a distributed ledger (e.g., an instance thereof) generates (or updates) a record corresponding to the user using the medical status and the attestation to the status. For example, the distributed ledger can generate the record to include one or more data entries that include an attribute type of the attribute, a hashed and encrypted value of the attribute, an attestor signature of the hashed and encrypted value of the attribute, and an address of the attestor. For example, the attribute of a data entry can be a medical status, such as a pass status (e.g., first value) indicating that the user is immune to or has been treated for or vaccinated for the medical condition, or a fail status (e.g., second value) indicating that user is not immune to, has not been treated for, or has not been vaccinated for the medical condition. The distributed ledger can perform at least one of a hash operation and an encryption operation on the medical status. The distributed ledger can generate or update the record responsive to requesting data from a health record database, such as part of a periodic update request, or responsive to receiving the data without a request.

At 1520, a wallet of the user receives credential data representative of the medical status of the user. The wallet can be implemented by a user device, such as a smartphone, operated by the user. The wallet can be an identity wallet operated by an application executed by the user device. The wallet can be physical device, such as a card, that presents the credential data. The credential data can include a representation of the medical status of the user. The wallet can receive the credential data responsive to receiving a request for the credential data from an access controller or from user input received at the application executed by the user device.

At 1525, the user device presents an indication of the credential data to indicate the medical status of the user. The user device can present the indication so that an entity associated with entry into a space, such as an administrator of the space or access control system that selectively permits entry into the space, can validate access into the space using the credential data. The user device can present the indication to include at least one of a visual representation and an audio representation of the medical status. For example, the user device can present text, colors, audio, or other information to represent the medical status. The user device can transmit an electronic signal that includes the indication for reception by a remote device, such as an access controller.

At 1530, access into the space is validated using the medical status of the user. For example, responsive to detecting that the medical status is a pass status (e.g., the user has been tested to be immune to, has been treated for, or has been vaccinated for the medical condition), access can be validated. Responsive to detecting that the medical status is not a pass status, an action can be performed to prevent access into the space, such as to output an error, or change or maintain a lock or other access control device to a lock state.

In some embodiments, the access control system can keep a count of users who are validated using the medical status of the users. The access control system can be structured to permit access into the space for users who do not have a medical status deemed to pass. In some embodiments, the access of users who do not have a passing medical status into the space can be based on a determined proportion of users in the space who have a passing medical status. For example, if the space is determined to have 85% or more of the users with a passing medical status, a person with a non-passing medical status (e.g., not vaccinated) may be permitted to access the space.

At 1535, at least one of the wallet and the distributed ledger can be updated responsive to the validation of the medical status. For example, the credential data maintained by the wallet can be updated to indicate that access was validated, and the wallet can transmit an indication that access was validated to the distributed ledger, which can update a time stamp associated with the medical status to indicate that access was validated (e.g., that the medical status was validated).

Figure 16:
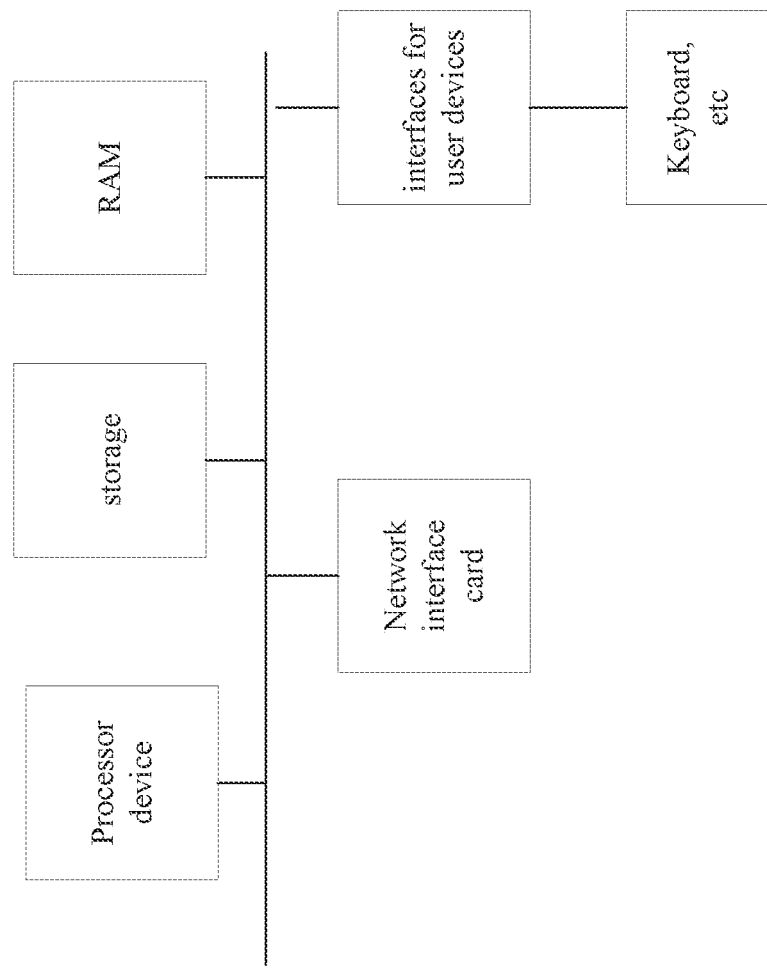
FIG. 16 is a block diagram of a computer system.

Referring now to FIG. 16, components of system/devices are shown. Memory stores program instructions and data used by the processor. The memory may be a suitable combination of random access memory and read-only memory, and may host suitable program instructions (e.g. firmware or operating software), and configuration and operating data and may be organized as a file system or otherwise. The program instructions stored in the memory may further store software components allowing network communications and establishment of connections to the data network. The software components may, for example, include an internet protocol (IP) stack, as well as driver components for the various interfaces. Other software components suitable for establishing a connection and communicating across network will be apparent to those of ordinary skill.

Servers are associated with an IP address and port(s) by which it communicates with user devices. The server address may be static, and thus always identify a particular one of monitoring server to the intrusion detection panels. Alternatively, dynamic addresses could be used, and associated with static domain names, resolved through a domain name service. The network interface card interfaces with the network to receive incoming signals, and may for example take the form of an Ethernet network interface card (NIC). The servers may be computers, thin-clients, or the like, to which received data representative of an alarm event is passed for handling by human operators. The monitoring station may further include, or have access to, a subscriber database that includes a database under control of a database engine. The database may contain entries corresponding to the various subscriber devices/processes to panels like the panel that are serviced by the monitoring station.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Computer program products are stored in a tangible form on non-transitory computer readable media and non-transitory physical hardware storage devices that are suitable for embodying computer program instructions and data. These include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory and other non-transitory devices.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced. Other substitutions, modifications, changes, and omissions may be made in the design, operating conditions and arrangement of embodiments without departing from the scope of the present disclosure.

As utilized herein, the terms "approximately," "about," "substantially", and similar terms are intended to include any given ranges or numbers +/−10%. These terms include insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. An access validation system, comprising:
one or more hardware processors that:
cause a distributed ledger to generate a record data structure regarding a first user, the record data structure comprising an attribute, the attribute being a medical status of the first user, the medical status indicating whether the first user has been tested for immunity to, has been treated for, or has been vaccinated for a medical condition;
update the record data structure periodically responsive to receiving data regarding the first user without a request, the updated record data structure comprising an updated medical status based on the data regarding the first user;
output credential data representing the updated medical status, wherein the credential data indicates a pass status indicating the first user is immune to or has been treated for or vaccinated for the medical condition or indicates a fail status indicating the first user is not immune to or has not been treated for or vaccinated for the medical condition;
determine whether the updated medical status complies with a policy associated with a space based on the credential data;
validate access of the first user into the space based on the credential data indicating the pass status and the updated medical status complying with the policy;
determine a proportion of users with access to the space based on the credential data indicating the pass status associated with each user in the proportion of users, the proportion of users including the first user;
validate access of a second user based on the proportion of users with access to the space crossing a threshold, the second user corresponding to a second updated medical status based on data regarding the second user, the second updated medical status including credential data indicating the fail status;
update the distributed ledger to indicate access was validated based on the updated medical status complying with the policy; and
the distributed ledger outputs the credential data responsive to verifying a request for the credential data based on a private key used to sign the request for the credential data.

2. The access validation system of claim 1, comprising:
the record data structure comprises an attribute type of the attribute, at least one of a hashed value and an encrypted value of the attribute, an attestor signature of the at least one of the hashed value and the encrypted value of the attribute, and an address of an entity that provides the attestor signature.

3. The access validation system of claim 1, comprising:
the distributed ledger outputs the credential data to an electronic identity wallet of a user device at least one of periodically and responsive to the request for the credential data.

4. The access validation system of claim 1, comprising:
the attribute is a first attribute, the record data structure comprises a second attribute indicating personally identifiable information of the first user, and the distributed ledger outputs the credential data to include the first attribute and not include the second attribute.

5. The access validation system of claim 1, comprising:
the distributed ledger receives an indication of validation of the medical status from an electronic wallet associated with the first user and updates the record data structure using the indication.

6. An access validation device, comprising:
a user interface that includes at least one of a display and an audio output device; and
one or more processors that:
cause an identity wallet to generate a credential regarding a medical status of a first user using credential data representative of the medical status received from a distributed ledger, the medical status indicating whether the first user has been tested for immunity to, has been treated for, or has been vaccinated for a medical condition; and
update the credential periodically responsive to receiving data regarding the first user without a request, the updated credential regarding an updated medical status based on the data regarding the first user;
present an indication of the updated medical status using the user interface, the indication indicating a pass status or a fail status, the pass status indicating the first user is immune to or has been treated for or vaccinated for the medical condition and the fail status indicating the first user is not immune to or has not been treated for or vaccinated for the medical condition;
receive an indication of validation of access into a space based the credential indicting a pass status and the updated medical status complying with a policy associated with the space;
determine a proportion of users with access to the space based on the credential data indicating the pass status associated with each user in the proportion of users, the proportion of users including the first user;
validate access of a second user based on the proportion of users with access to the space crossing a threshold, the second user corresponding to a second updated medical status based on data regarding the second user, the second updated medical status including credential data indicating the fail status;
transmit an update to a distributed ledger from which the credential data is received to update the distributed ledger based on the indication of the validation; and
the distributed ledger outputs the credential data responsive to verifying a request for the credential data based on a private key used to sign the request for the credential data.

7. The access validation device of claim 6, comprising:
the identity wallet presents the indication of the second updated medical status responsive to at least one of a user input received at the user interface and a request for the second updated medical status received from an access controller.

8. The access validation device of claim 6, comprising:
the identity wallet presents the indication of the second updated medical status by causing a wireless transmission of the indication of the second updated medical status to an access controller.

9. The access validation device of claim 6, comprising:
the identity wallet requests the credential data from a distributed ledger by signing the request for the credential data using at least one of the private key and a signature of the first user and transmitting the request for the credential data to the distributed ledger.

10. The access validation device of claim 6, comprising:
the identity wallet transmits a request for access into a space using the credential.

11. A method of validating access into a space, comprising:
- receiving, by an electronic device associated with a first user, a request to enter the space;
- identifying, by the electronic device, credential data indicating a medical status of the first user corresponding to a policy for entry into the space by the first user;
- updating the credential data periodically responsive to receiving data regarding the first user without a request, the updated credential data regarding an updated medical status based on the data regarding the first user;
- outputting, by the electronic device, a credential representing the updated credential data, the credential indicating a pass status or a fail status, the pass status indicating the first user is immune to or has been treated for or vaccinated for the medical condition and the fail status indicating the first user is not immune to or has not been treated for or vaccinated for the medical condition;
- receiving, by the electronic device, an indication of validation of access into the space based on the credential indicating a pass status and the updated medical status complying with the policy;
- determining, by the electronic device, a proportion of users with access to the space based on the credential data indicating the pass status associated with each user in the proportion of users, the proportion of users including the first user;
- validating, by the electronic device, access of a second user based on the proportion of users with access to the space crossing a threshold, the second user corresponding to a second updated medical status based on data regarding the second user, the second updated medical status including credential data indicating the fail status; and
- updating, by the electronic device, a distributed ledger that maintains the updated credential data responsive to receiving the indication of validation of access into the space, wherein the distributed ledger outputs the credential data responsive to verifying a request for the credential data based on a private key used to sign the request for the credential data.

12. The method of claim 11, comprising:
receiving, by the electronic device, the request for the credential data as a first wireless signal from an access controller; and
outputting, by the electronic device, the credential as at least one of a visual representation of the credential, an audio representation of the credential, and a second wireless signal for reception by the access controller.

13. The method of claim 11, comprising:
receiving, by the electronic device, the credential data from a distributed ledger that maintains a record data structure comprising an attribute type of an attribute that comprises the second updated medical status, at least one of a hashed value and an encrypted value of the attribute, an attestor signature of the at least one of the hashed value and the encrypted value of the attribute, and an address of an entity that provides the attestor signature.

14. The method of claim 11, comprising:
generating, by a distributed ledger, the credential data using information received from at least one of a medical entity and a government entity.

* * * * *